United States Patent
Masters et al.

(10) Patent No.: US 11,716,577 B2
(45) Date of Patent: Aug. 1, 2023

(54) ULTRASOUND TRANSDUCER AND HOUSING FOR SAME

(71) Applicant: Cybersonics, Inc., Erie, PA (US)

(72) Inventors: Jonathan C. Masters, Panama, NY (US); Geoffrey Bond, Erie, PA (US)

(73) Assignee: Cybersonics, Inc., Erie, PA (US)

( * ) Notice: Subject to any disclaimer, the term of this patent is extended or adjusted under 35 U.S.C. 154(b) by 517 days.

(21) Appl. No.: 16/993,911

(22) Filed: Aug. 14, 2020

(65) Prior Publication Data
US 2021/0051416 A1 Feb. 18, 2021

Related U.S. Application Data

(60) Provisional application No. 62/887,027, filed on Aug. 15, 2019.

(51) Int. Cl.
| | |
|---|---|
| *A61N 7/00* | (2006.01) |
| *H04R 17/10* | (2006.01) |
| *G10K 11/00* | (2006.01) |
| *B06B 1/06* | (2006.01) |

(52) U.S. Cl.
CPC ............... *H04R 17/10* (2013.01); *A61N 7/00* (2013.01); *B06B 1/0651* (2013.01); *G10K 11/004* (2013.01); *A61N 2007/0056* (2013.01)

(58) Field of Classification Search
CPC .............. A61N 2007/0056; A61N 7/00; B06B 1/0238; B06B 1/0611; B06B 1/0651; B06B 1/0666; B06B 2201/76; G10K 11/004; H04R 17/10; H04R 31/006; A61B 2090/064
See application file for complete search history.

(56) References Cited

U.S. PATENT DOCUMENTS

| | | |
|---|---|---|
| 3,735,159 A | 5/1973 | Murry |
| RE33,977 E | 6/1992 | Goodman et al. |
| 5,998,908 A | 12/1999 | Goodson |
| 6,288,476 B1 | 9/2001 | Puskas |
| 8,585,597 B2 | 11/2013 | Dae et al. |
| 2004/0073115 A1 | 4/2004 | Horzewski et al. |
| 2006/0173321 A1 | 8/2006 | Kubota et al. |
| 2007/0080609 A1 | 4/2007 | Johnson et al. |
| 2010/0208553 A1 | 8/2010 | Massa |
| 2011/0285244 A1 | 11/2011 | Lewis et al. |
| 2016/0325311 A1 | 11/2016 | Vaitekunas et al. |

FOREIGN PATENT DOCUMENTS

WO 2016127158 A1 8/2016

OTHER PUBLICATIONS

Copenheaver, Blaine R.; International Search Report and Written Opinion of the International Searching Authority issued in International Application No. PCT/US2020/048392; dated Nov. 23, 2020; 13 pages.
Copenheaver, Blaine R.; International Search Report and Written Opinion of the International Searching Authority issued in International Application No. PCT/US2020/046391; dated Dec. 16, 2020; 14 pages.

*Primary Examiner* — Mark D Remaly
(74) *Attorney, Agent, or Firm* — Ulmer & Berne LLP; Brian E Turung; Anthony R. Tomusko

(57) ABSTRACT

An ultrasound energy delivery system is provided that includes a transducer and a housing.

23 Claims, 22 Drawing Sheets

ULTRASOUND TRANSDUCER AND HOUSING FOR SAME

REFERENCE TO RELATED APPLICATIONS

This application claims priority to U.S. Provisional Patent Application Ser. No. 62/887,027, filed Aug. 15, 2019, and hereby incorporates this application by reference in its entirety.

TECHNICAL FIELD

The apparatuses and methods described below relate to a transducer for an ultrasound system and a housing for the transducer.

BACKGROUND

Chronic kidney disease affects millions of patients and has shown an increased prevalence in recent years. End-stage kidney disease alone affects hundreds of thousands of patients, and the numbers of these patients may double within the next 15 years. Chronic renal diseases can be complicated by progressive fibrosis and deterioration of renal function and often, ultimately, results in irreversible renal failure. Treatment options for end-stage renal diseases typically involve repeated and time consuming dialysis procedures or kidney transplantation.

While much of the alarming increase in chronic and end-stage kidney disease relates to the rise in prevalence of obesity, diabetes, hypertension, and other cardiovascular risk factors, the kidneys are also subject to injury from additional sources. Acute kidney injury related to imaging procedures in which contrast media is administered to the patient appears to be one of the leading causes of hospital acquired renal failure. The deleterious effects of contrast media on the kidneys may be linked to increased lengths of hospital stays, higher rates of in-hospital cardiovascular events and increased mortality. Patients with pre-existing renal dysfunction and microvascular insufficiency are particularly vulnerable to the dangers of contrast-induced injury to the kidneys. Unfortunately, the population of patients with compromised kidneys that may be placed at risk by imaging procedures includes many of the same individuals whose lives may be saved and/or improved through the benefits of interventional cardiovascular and other therapies that are made possible through the use of contrast-enhanced imaging. As a result, millions of patients may be at risk for contrast-induced acute or chronic kidney injury.

Attempts to reduce or prevent contrast medium-induced renal failure have included periprocedural hydration, forced diuresis, blood volume expansion, low osmolality versus high osmolality contrast agents, dopamine, calcium channel blockers, mannitol, atrial natriuretic peptide, acetylcholine esterase (ACE) inhibitors, adenosine antagonist theophylline, endothelin receptor antagonists, N-acetylcysteine, as well as the use of alternative contrast agents, such as carbon dioxide. None of these attempts has been fully effective. Contrast induced acute kidney injury, including Contrast-Induced Nephropathy (CIN), remains a leading cause of iatrogenic acute kidney injury, despite adherence to protocols of risk assessment and prevention strategies. CIN in particular, involves the impairment of renal function—measured as either a 25% increase in serum creatinine (SCr) from baseline or a 0.5 mg/dL (44 µmon) increase in absolute SCr value—within 48-72 hours after intravenous contrast administration.

In light of the above, it would be beneficial to provide improved devices, systems, and methods for treating patients. It would be particularly beneficial if these improved structures and techniques could be used to help mitigate the injury suffered by the kidneys of patients having chronic and/or acute renal disease. It would also be desirable for such benefits to be provided without excessively increasing the time and costs of life-preserving dialysis treatments, while helping to maintain (or even increase) the quality of life of dialysis patients.

Additionally, there remains an unmet need for a device that can reduce the incidence of Contrast Induced Nephropathy (CIN).

Further, there remains an unmet need for a transcutaneous ultrasound product that can be utilized by interventional cardiologists and interventional radiologists while performing cardiovascular catheterizations.

BRIEF DESCRIPTION OF THE DRAWINGS

The following detailed description of embodiments can be best understood when read in conjunction with the drawings enclosed herewith.

DETAILED DESCRIPTION

Figure 1:
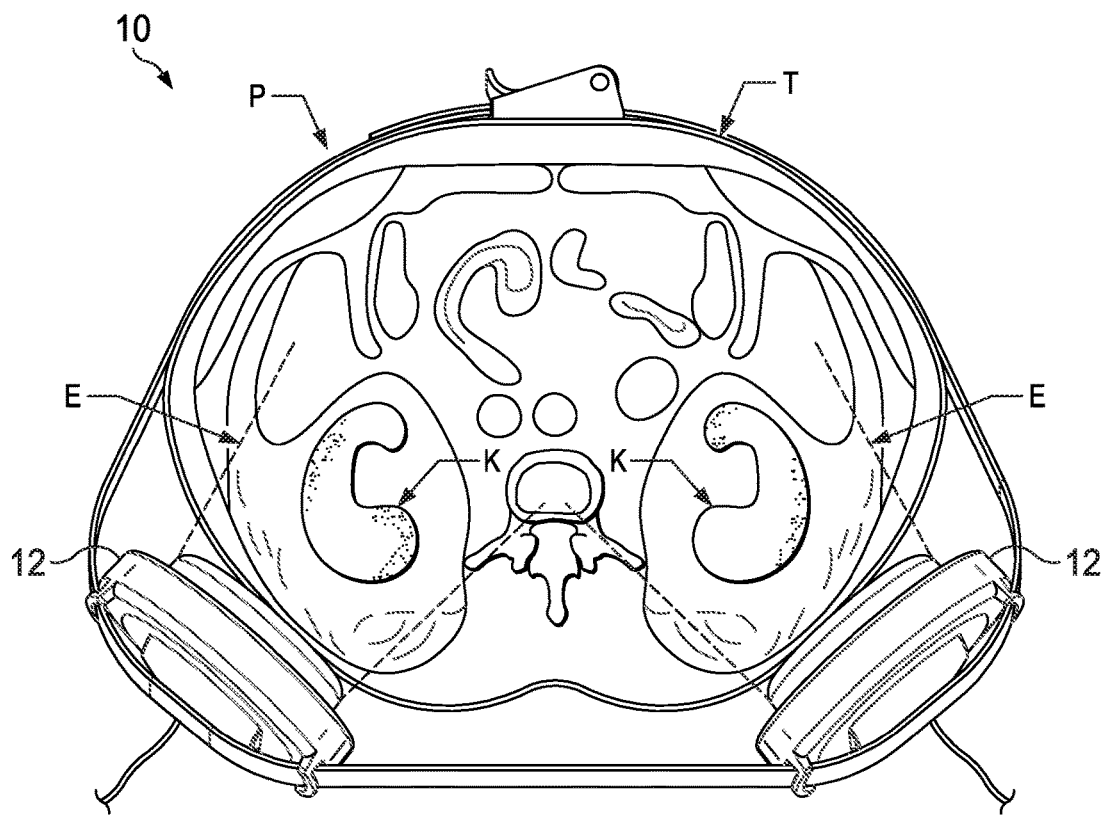
FIG. 1 is a cross-sectional view depicting a patient's torso in association with an ultrasound energy delivery system that includes two transducers each directing ultrasonic energy to the patient's kidneys.

The various embodiments described below are generally directed to transcutaneous ultrasound transducers that can be utilized in any of a variety of medical applications to perform an ultrasound on tissues or internal organs, such as a heart or a kidney, for example. The structures and techniques provided often employ cyclical mechanical pressure energy, most often in the form of non-ablative low frequency ultrasound energy. The energy may be at energy levels that are sufficiently low that no therapeutically significant heating of the tissues is generated, but with the energy penetrating into target tissues at levels that are sufficient to induce shear stress. As such, the energy levels are sufficiently low so as to be safe for intervening tissues between the target tissue and the transducer, such that the therapeutic energy can be transmitted from outside of the patient's body, through the skin and any intervening tissues so as to access the target tissues and provide therapeutic benefits without imposing trauma.

The devices, products, and methods described herein may be employed to treat a variety of tissue structures so as to ameliorate a wide variety of disease states. Certain embodiments may be particularly well suited for treatment of diseases that include an ischemic component, including coronary artery disease, occlusive diseases of the peripheral vasculature, erectile dysfunction, hypertension, diabetes, and the like. The exemplary embodiments may have their most immediate application for treatment of the kidneys. Such embodiments may ameliorate, mitigate, and/or avoid some or all acute or long term injury to tissues of the kidneys. Many of the embodiments may be described herein with reference to inhibiting injury to the kidneys associated with administration of contrast imaging agents prior to and/or in conjunction with dialysis treatment so as to inhibit progression of chronic kidney disease. Additionally, the structures and techniques described for these indications will often be suitable for other therapies as can be understood with reference to the disclosure herein.

Ultrasound is cyclic sound pressure with a frequency greater than the upper limit of human hearing, which is approximately 20 kHz. Preliminary data has been obtained to show the effects of external application of pulsed low frequency ultrasound (LOFUS) in the range of 29 kHz, with an on-off duty cycle of 30%, and power level of 0.4 w/cm2 on myocardial blood flow in patients with regional rest and stress induced ischemia.

The embodiments described below can include the external application of low frequency ultrasound to protect the kidney against injury by inducing shear stress and causing phosphorylation of endothelial nitric oxide synthase to increase the production and release of NO in the kidney prior to, during, or following the administration of toxic nephrotoxic substances, such as radiocontrast media. One example is to apply LOFUS prior to, during, and or following the administration of contrast material to patients undergoing CT imaging of various organs. Application of LOFUS may occur with the patient sitting, lying supine, or lying in the prone position. Another example is to apply LOFUS prior to, during, or following the administration of contrast media to patients undergoing diagnostic or therapeutic angiographic procedures in the catherization laboratory, including cardiac and interventional radiology.

An ultrasound energy delivery system 10 (hereinafter "the system") is illustrated in FIG. 1 and is shown to include a pair of transducers 12. The transducers 12 can be placed on a torso T of a patient P and configured to supply ultrasonic energy E towards the kidneys K of the patient P, oftentimes without the measurement of a reflection signature for use in imaging. The ultrasonic energy E can be unfocused, nonablative LOFUS energy and can facilitate treatment against various different acute or chronic injuries. Each of the transducers 12 can be controlled separately or simultaneously with each other.

Figure 2:
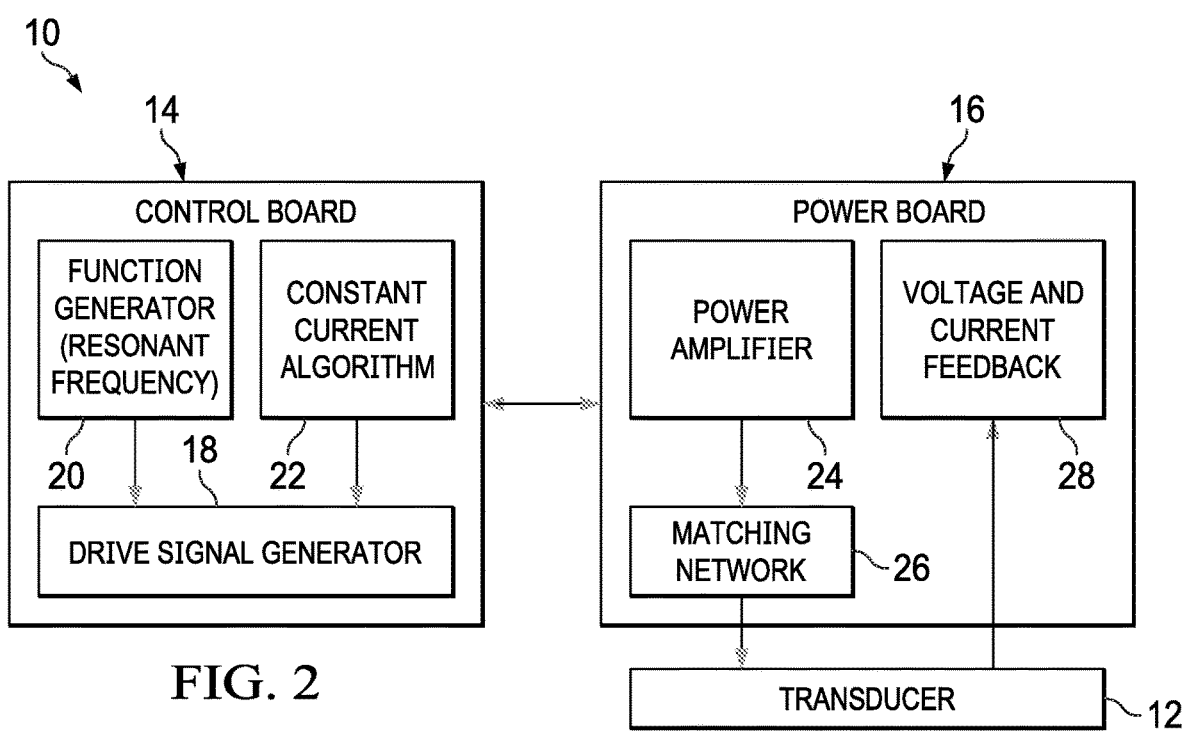
FIG. 2 is a schematic view of the ultrasound energy delivery system of FIG. 1.

Referring now to FIG. 2, the system 10 can include a control board 14 and a power board 16. The control board 14 can include a drive signal generator 18 that is configured to generate a drive signal that is provided to the power board 16 for transmission to the transducers 12. The control board 14 can include a function generator 20 and a constant current algorithm module 22 that cooperate with the drive signal generator 18 to generate the drive signal with distinct signal characteristics (e.g., modulation frequency and duty cycle). In one embodiment, the function generator 20 can comprise an Agilent 33220 sine wave generator. The drive signal generator 18 can be in signal communication with a power amplifier 24 of the power board 16 such that the drive signal can be provided from the control board 14 to the power board 16. The power board 16 can include a matching network 26 that cooperates with the power amplifier 24 to condition the amplified drive signal from the power amplifier 24 for transmission to the transducer 12. The control board 14 can also include a feedback module 28 that receives a feedback signal from the transducers 12 to facilitate real time control of the transducers 12.

The system 10 is shown in FIG. 2 to include an individual drive signal for driving the transducers 12. The individual drive signal can be multiplexed in coordination with a micro and/or macro duty cycle, or the like, to facilitate powering of the transducers 12 together. In an alternative embodiment, the transducers 12 can be driven by different drive signals (generated by different function generators). It is to be appreciated that any of a variety of suitable alternative system architectures can be employed for driving the transducers 12.

Figure 3:
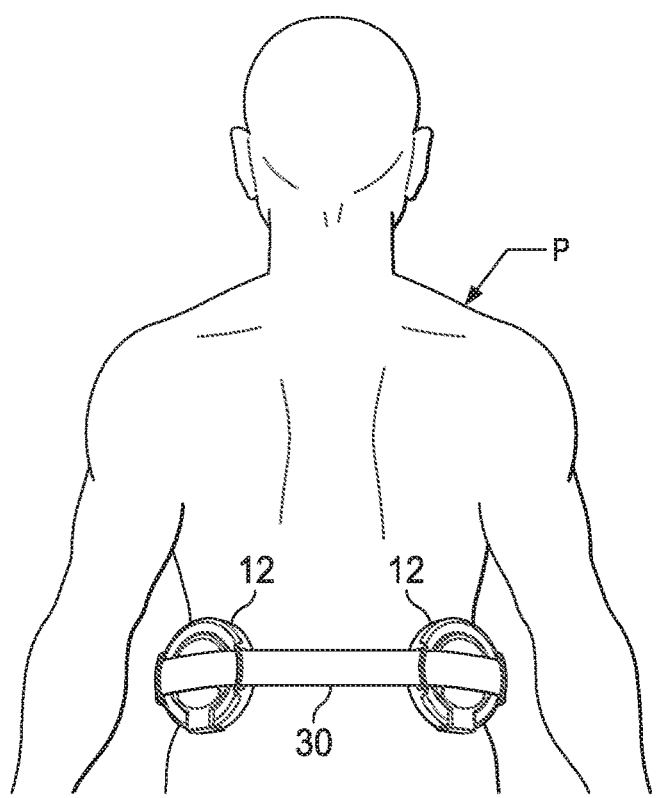
FIGS. 3-5 are different views depicting a belt worn by a patient for orienting the transducers of the ultrasound energy delivery system of FIG. 1 towards a patient's kidneys.
Figure 4:
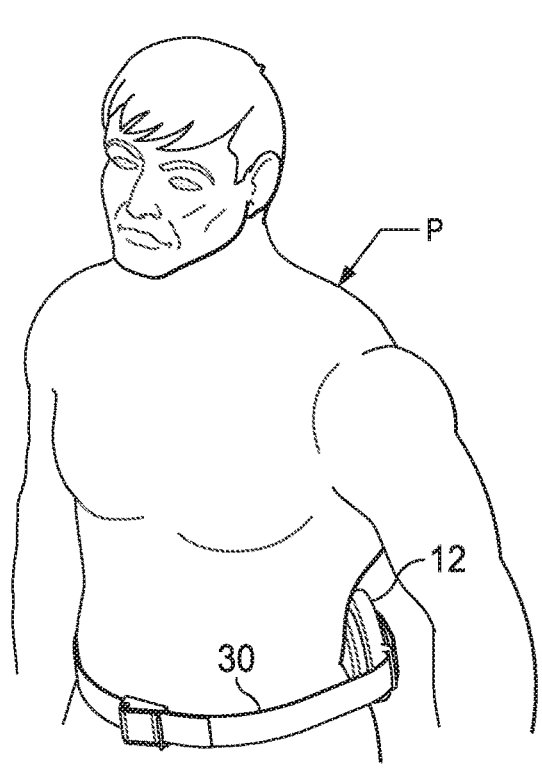
Figure 5:
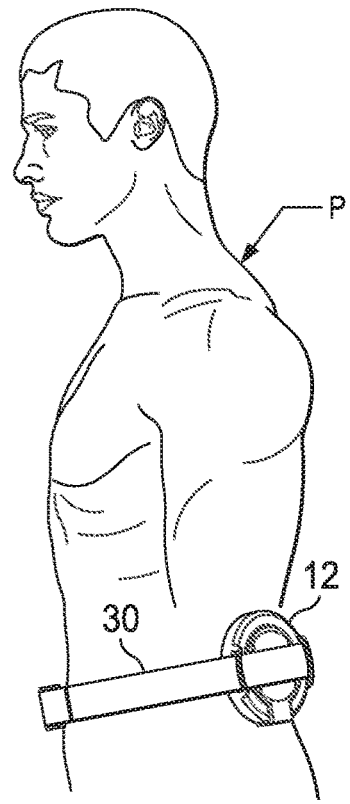

Referring now to FIGS. 3-5, in one embodiment, the transducers 12 are shown to be provided in a belt 30 that can be worn by the patient P during an ultrasonic treatment. The belt 30 can allow for mobility of the patient P during treatment while maintaining alignment between the patient P and the transducers 12. In another embodiment, the transducers 12 can be mounted within a table (not shown) such that the transducers 12 can be located adjacent the kidneys K of the patient P when the patient P is laying on the table. It is to be appreciated that the transducers 12 can be provided in any of a variety of suitable alternative support structures that facilitate location of the transducers 12 relative to a patient during an ultrasonic treatment. When used to ameliorate injury from contrast media, the support structure can be configured to accommodate imaging through an imaging window (such as an opening or material that is transparent for imaging through). The treatment may be done acutely prior to, during, or following administration of toxic substances such as contrast media, or the treatments may be done over a prolonged period of time, including but not limited to minutes, days, weeks, or months. The system may be used to treat one type of organ, such as the kidneys K, while providing protection for a remote organ, such as the brain, liver, or heart.

Figure 6A:
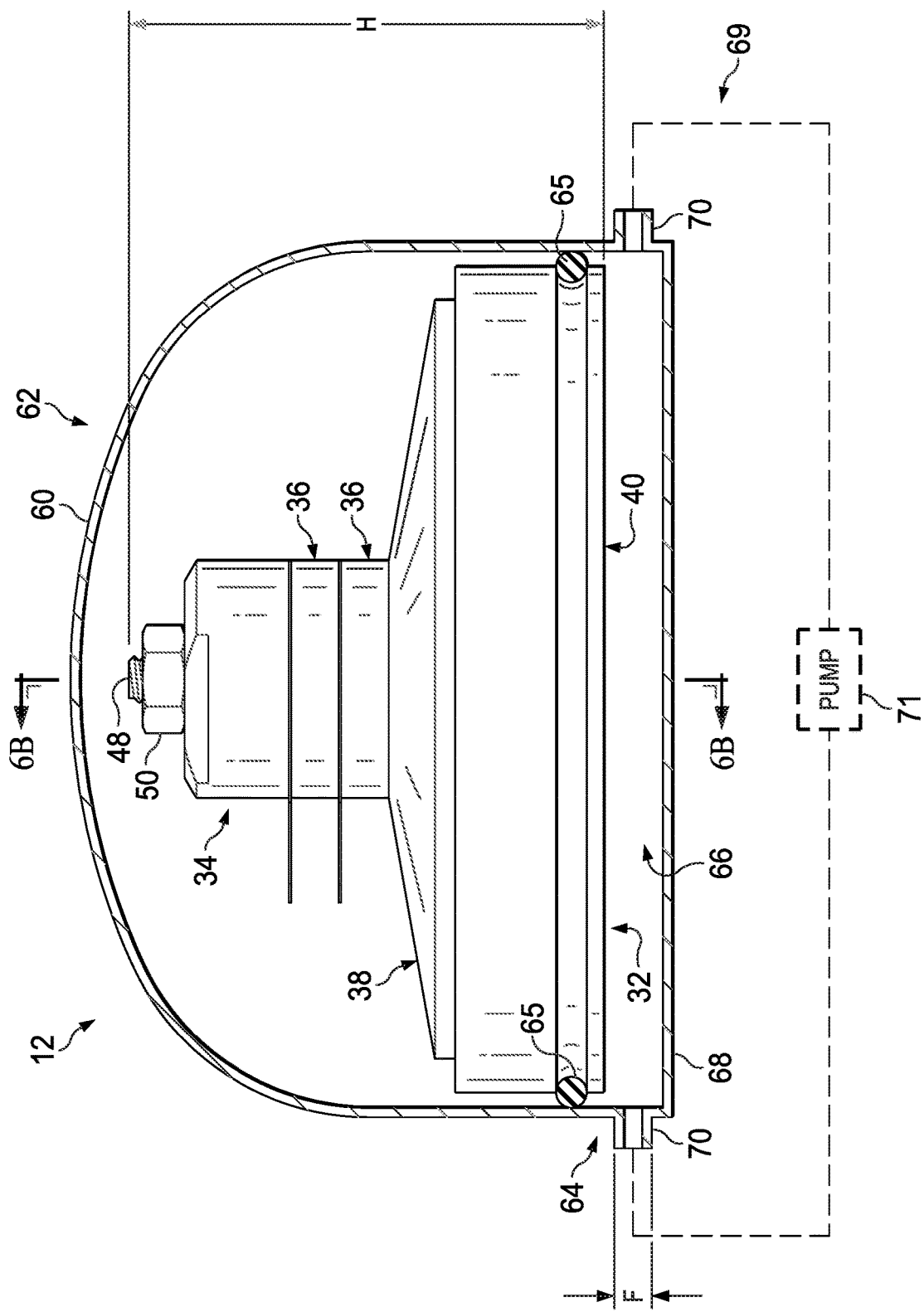
FIG. 6A is a side view depicting the transducer of FIG. 1 in association with a housing and a recirculation system, in accordance with one embodiment.
Figure 6B:
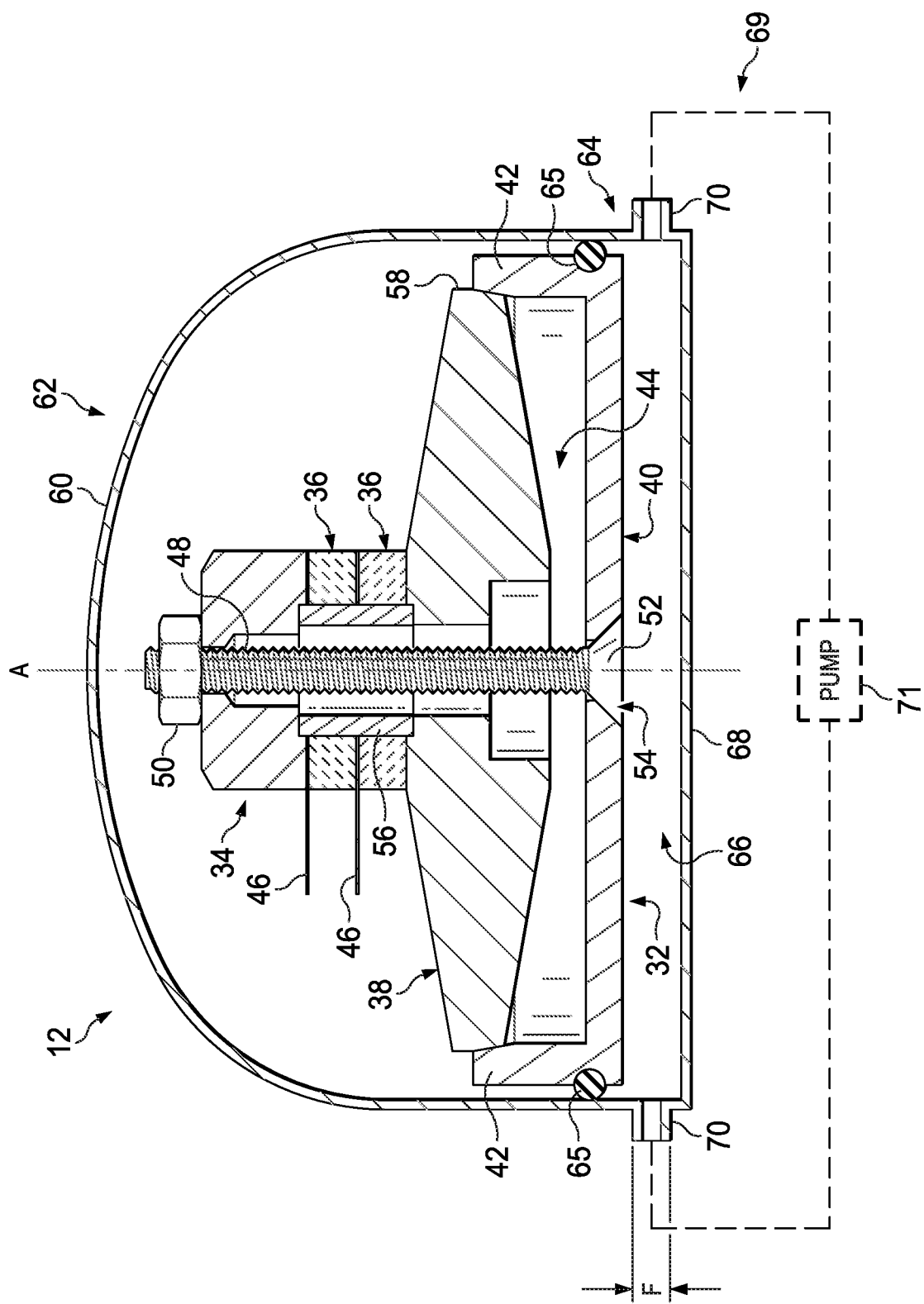
FIG. 6B is a cross sectional view taken along the line 6B-6B in FIG. 6A.

Referring now to FIGS. 6A and 6B, one of the transducers 12 is illustrated and will be described herein, but can be understood to be representative of both transducers 12. The transducer 12 can include a frontmass 32, a backmass 34, a pair of piezoelectric rings 36 and a shim 38. The piezoelectric rings 36 (e.g., annular rings) can be sandwiched between the shim 38 and the backmass 34. The frontmass 32 can include a radiating portion 40 and a sidewall 42 that extends upwardly from the radiating portion. As illustrated in FIG. 6B, the shim 38 can be coupled with the sidewall 42 and spaced from the radiating portion 40 such that the shim 38 and the radiating portion 40 cooperate to define an interior chamber 44. In one embodiment, the shim 38 and the sidewall 42 can be coupled together in an interference fit along an outer perimeter of the shim 38.

The piezoelectric rings 36 can be electrically coupled to the drive signal generator 18 (FIG. 2) via a pair of electrodes 46 that are each electrically coupled with respective ones of the piezoelectric rings 36. The piezoelectric rings 36 can be formed of a piezoelectric material such as piezoceramic, which can resonate (e.g., generate ultrasonic energy) in response to the driving signal imparted thereto by the drive signal generator 18. It is to be appreciated that, although a pair of piezoelectric rings are illustrated, any quantity of piezoelectric rings are contemplated (one piezoelectric ring or more than two piezoelectric rings).

A fastener 48 (e.g., a screw or a bolt) can extend through each of the frontmass 32, the piezoelectric rings 36, the shim 38 and the backmass 34 and can define a centerline A such that the frontmass 32, the backmass 34, the piezoelectric rings 36, and the shim 38 are aligned coaxially along the centerline A. The fastener 48 can be threadably coupled with a nut 50 to compress the frontmass 32, the piezoelectric rings 36, the shim 38 and the backmass 34 together along the centerline A. The fastener 48 can have a head 52 that can be configured to reside in a countersunk depression 54 defined by the frontmass 32, such that the radiating portion 40 and the head 52 cooperate to define a generally planar surface. An insulator 56 can be interposed between each of the piezoelectric rings 36 and the fastener 48 and configured to electrically isolate the piezoelectric rings 36 from the fastener 48 while permitting vibration from the piezoelectric rings 36 to be transmitted to the fastener 48. In one embodiment, the insulator 56 can be formed of a phenolic material. In an alternative embodiment, the fastener 48 can be threaded directly into the backmass 34 in lieu of the nut 50.

The fastener 48 and the nut 50 can cooperate to compress the frontmass 32, the piezoelectric rings 36, the shim 38 and the backmass 34 together with enough force to permit the ultrasonic energy from the piezoelectric rings 36 to be transmitted through the fastener 48 to the radiating portion 40 and through the shim 38 and the sidewall 42 to the radiating portion 40 to collectively cause the radiating portion 40 to resonate with ultrasonic energy at a flexural resonance and frequency (as defined by the ultrasonic energy from the piezoelectric rings 36).

The shim 38 can have a tapered profile (e.g., a shape that tapers radially outwardly from the centerline A when viewed from a direction that is perpendicular to the centerline A), which can effectively funnel and amplify the ultrasonic energy from the piezoelectric rings 36 towards the outer circumference of the shim 38. The shim 38 can include a peripheral surface 58 that is beveled and engages the frontmass 32 (e.g., via an interference fit) in such a manner that enhances the transmission of the ultrasonic energy from the shim 38 to the frontmass 32. Since the shim 38 is spaced from the radiating portion 40 (e.g., by the interior chamber 44), the shim 38 can therefore separate the piezoelectric rings 36 from direct contact with the radiating portion 40 while also providing a transmission path for the ultrasonic energy from the piezoelectric rings 36 to the frontmass 32 such that the frontmass 32 facilitates generation of ultrasonic energy at a flexural resonance and frequency defined by the driving signal.

The shim 38 and the frontmass 32 can be tuned to facilitate effective transmission of the ultrasonic energy from the piezoelectric rings 36 to generate a desired vibrational pattern/flexural resonance (e.g., of nodes and antinodes) on the radiating portion 40. In one embodiment, the shim 38 and the frontmass 32 can be formed of aluminum. It is to be appreciated, however, that the shim 38 and the frontmass 32 can be formed of any of a variety of suitable alternative materials.

Still referring to FIGS. 6A and 6B, the transducer 12 can be housed in a housing 60 that includes an upper portion 62 and a lower portion 64. An O-ring 65 can be disposed between the housing 60 and the frontmass 32 to provide a sealing interface therebetween such that the lower portion 64 and the frontmass 32 cooperate to define a fluid chamber 66. The radiating portion 40 can accordingly be disposed in the fluid chamber 66. The lower portion 64 can include a patient interface 68 that is spaced from the radiating portion 40 by a fluid depth F and configured to interface with a patient's skin during treatment. In one embodiment, the patient interface 68 can be spaced from the radiating portion 40 by a fluid depth F that is a multiple of a quarter wavelength of sound in the coupling fluid at the frequency of the flexural resonance of the radiating portion 40. The fluid chamber 66 can retain a cooling medium (e.g., coupling fluid) that promotes transmission of the ultrasonic energy from the radiating portion 40 to the patient interface 68 while simultaneously cooling the radiating portion 40 (e.g., to prevent overheating) and the patient interface 68 (e.g., to prevent the patient from being burned). The patient interface 68 can comprise a relatively rigid interface or a relatively compliant membrane, can be flat or curved, and can comprise an elastomeric, rigid thermoplastic, or metal material. In one embodiment, the patient interface 68 can comprise a polymeric membrane to provide an enhanced dielectric barrier between the patient and the voltage applied to the transducer 12. In such an arrangement, the transducer 12 can provide higher thermal and electrical insulation, better control of fluid depth F between the transducer 12 and the patient, and more effective reusability and cleanability than conventional arrangements (e.g., rubber membranes).

The fluid chamber 66 can be fluidly coupled with a recirculation system 69 (shown in dashed lines) via fluid ports 70. The recirculation system 69 can include a pump 71 that circulates the cooling medium through the fluid chamber 66 to facilitate the removal of heat from the fluid chamber 66 by cooling the fluid medium.

It is to be appreciated that the stacked arrangement of the backmass 34, the piezoelectric rings 36, the shim 38, and the frontmass 32 can result in the transducer 12 being more compact and lightweight than conventional arrangements without sacrificing performance. As such, the transducer 12 can be more versatile, easier to use and more energy efficient. The more compact design will allow the device to be applied beneath the patient without significant discomfort. The lighter weight of the design will increase the comfort of the patient when the device must be applied for long durations.

Figure 7:
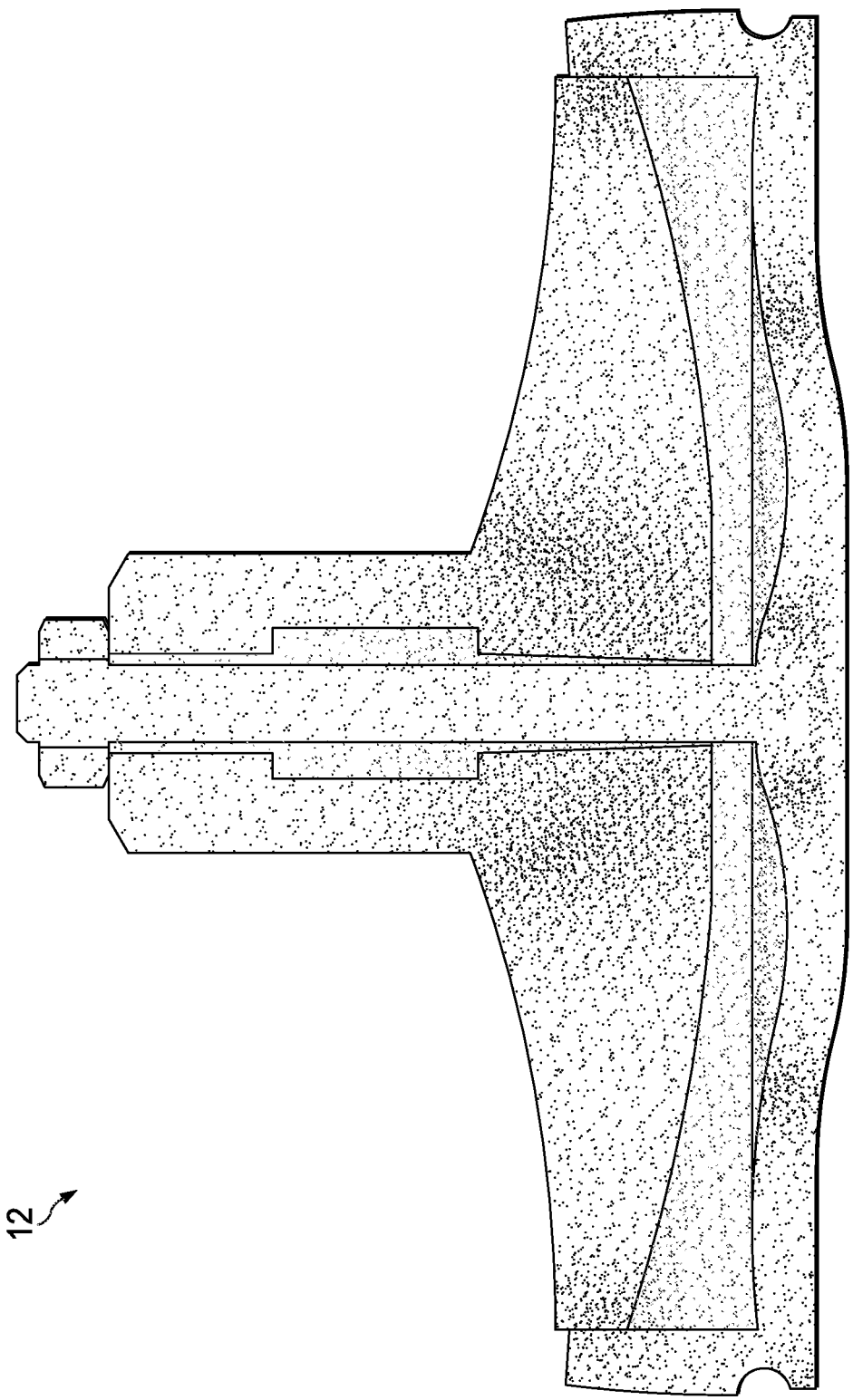
FIGS. 7 and 8 are a cross sectional view and a bottom view, respectively, depicting a propagation of vibration through the transducer of FIGS. 6A and 6B.
Figure 8:
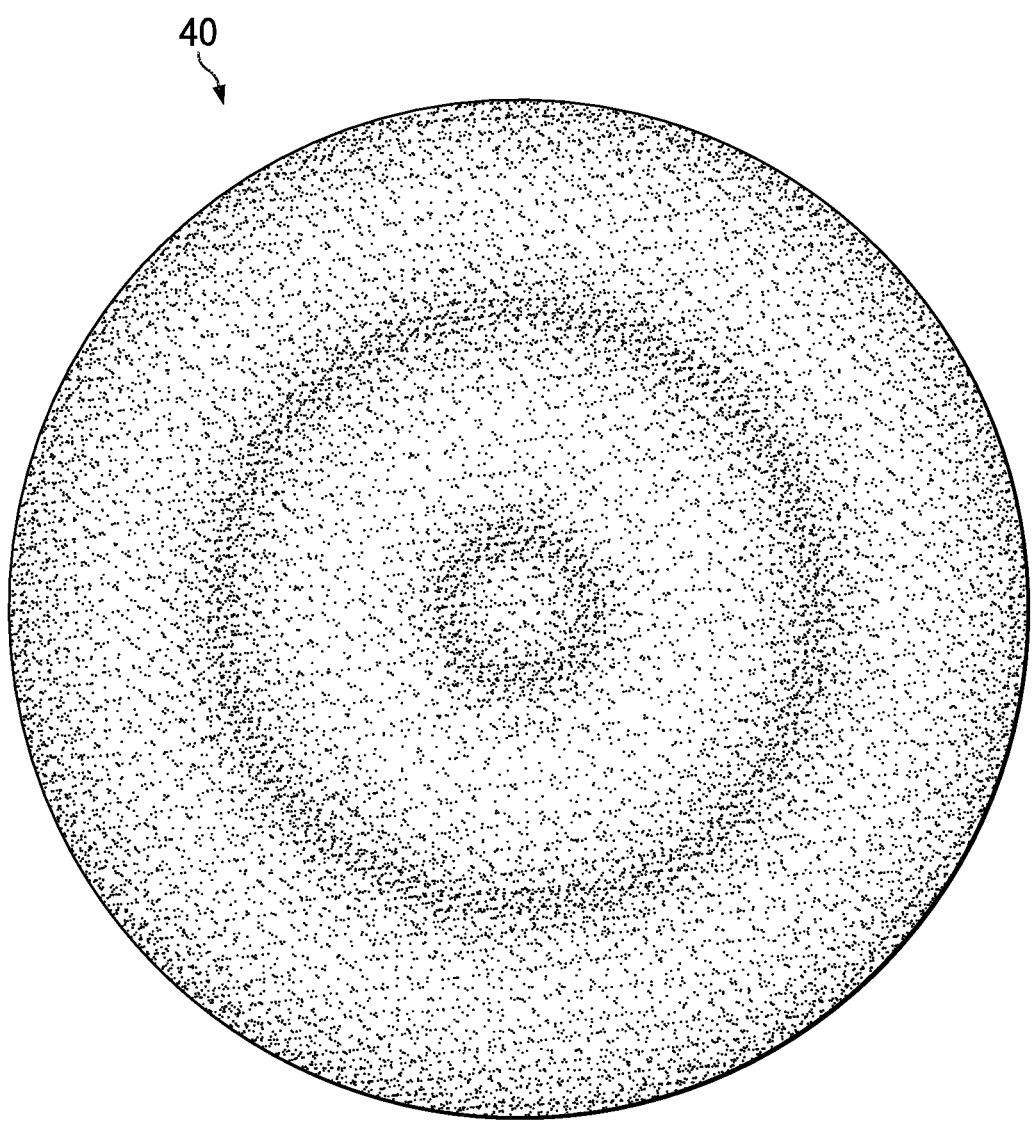

In one embodiment, the radiating portion 40 of the frontmass 32 can be tuned to the same frequency as the longitudinal mode of the transducer 12 or, alternatively, tuned away from the longitudinal mode. If the flexural resonance of the frontmass 32 is tuned to the longitudinal mode, there can be an antinode at a center of the radiating portion 40. If the flexural resonance is sufficiently far from the longitudinal mode, there can be a node at the center of the radiating portion 40. FIGS. 7 and 8 illustrate one example of the propagation of the vibration through the transducer 12 (FIG. 7) to create nodes and antinodes on the radiating portion 40 (FIG. 8). In one embodiment, the frontmass 32 can be tuned to an intermediate frequency such that a subdued antinode is present at the radiating portion 40.

Figure 9A:
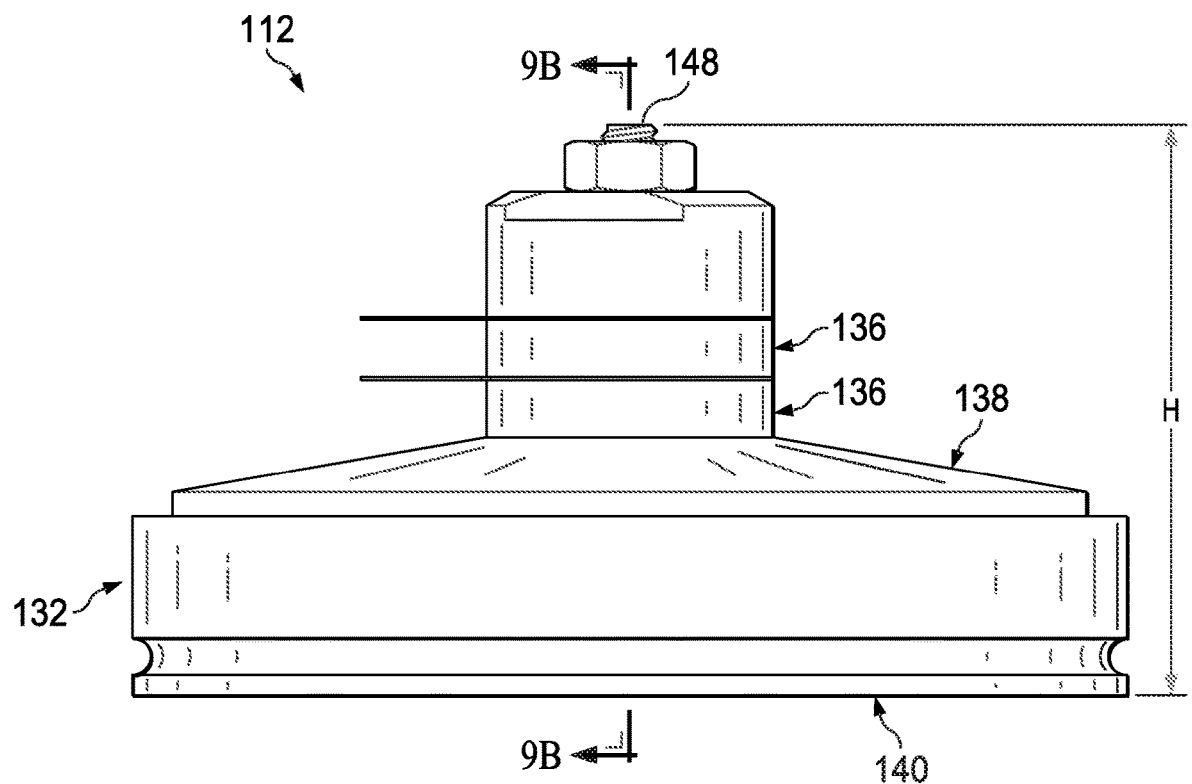
FIG. 9A is a side view depicting a transducer, in accordance with another embodiment.
Figure 9B:
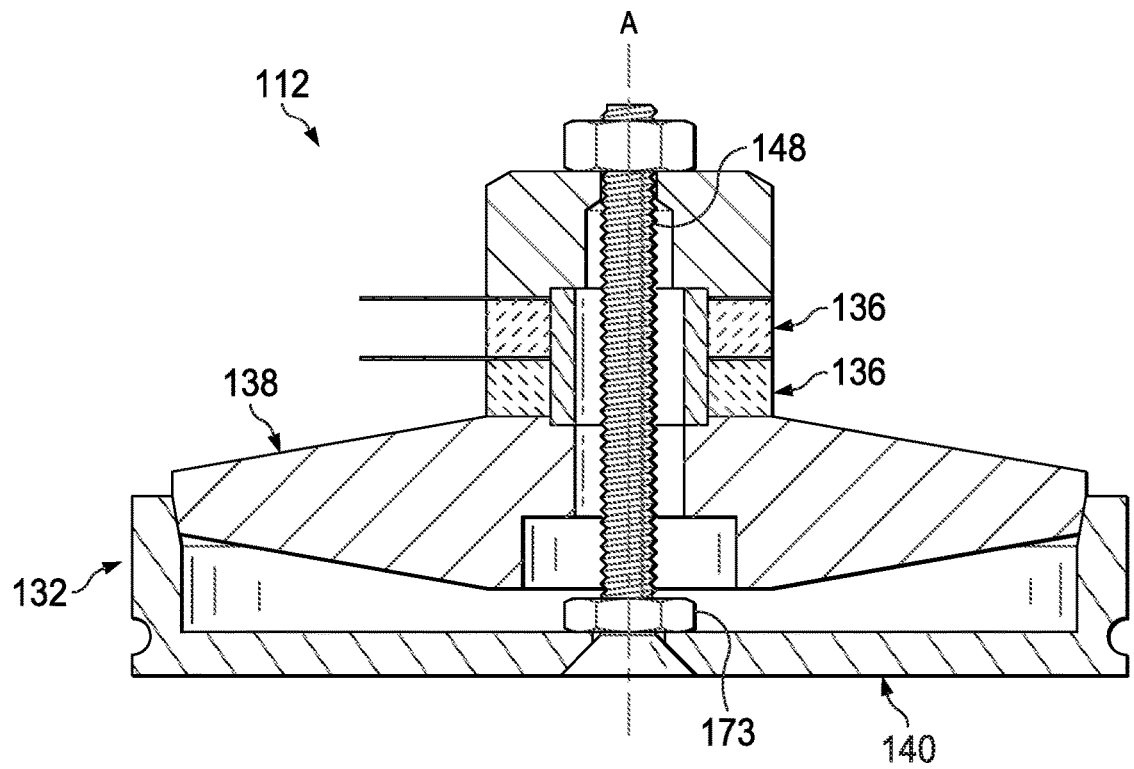
FIG. 9B is a cross sectional view taken along the line 9B-9B in FIG. 9A.

FIGS. 9A and 9B illustrate an alternative embodiment of a transducer 112 that is similar to, or the same in many respects as, the transducer 12 illustrated in FIGS. 6A and 6B. For example, the transducer 112 can include a frontmass 132, piezoelectric rings 136, a shim 138, and a fastener 148. However, the transducer 112 can include a nut 173 that is threaded on the fastener 148 against the shim 138. The nut 173 can be interposed between the shim 138 and a radiating portion 140 of the frontmass 132 and can facilitate securement of the fastener 148 to the radiating portion 140.

Figure 10A:
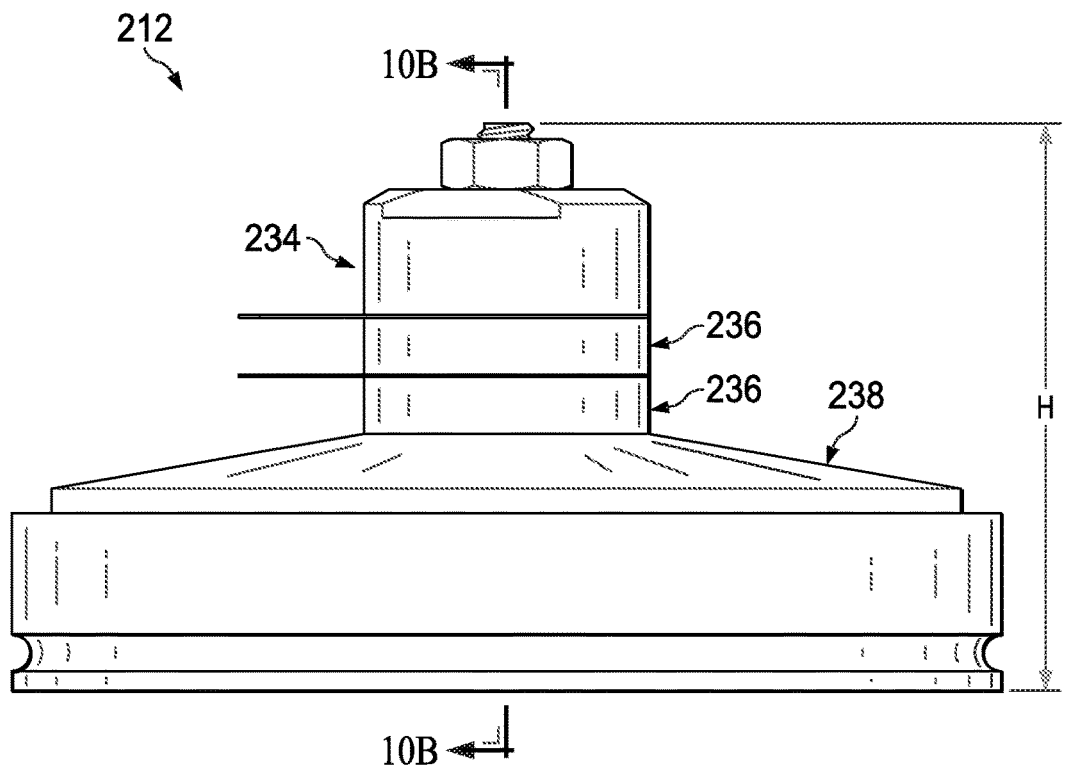
FIG. 10A is a side view depicting a transducer, in accordance with yet another embodiment.
Figure 10B:
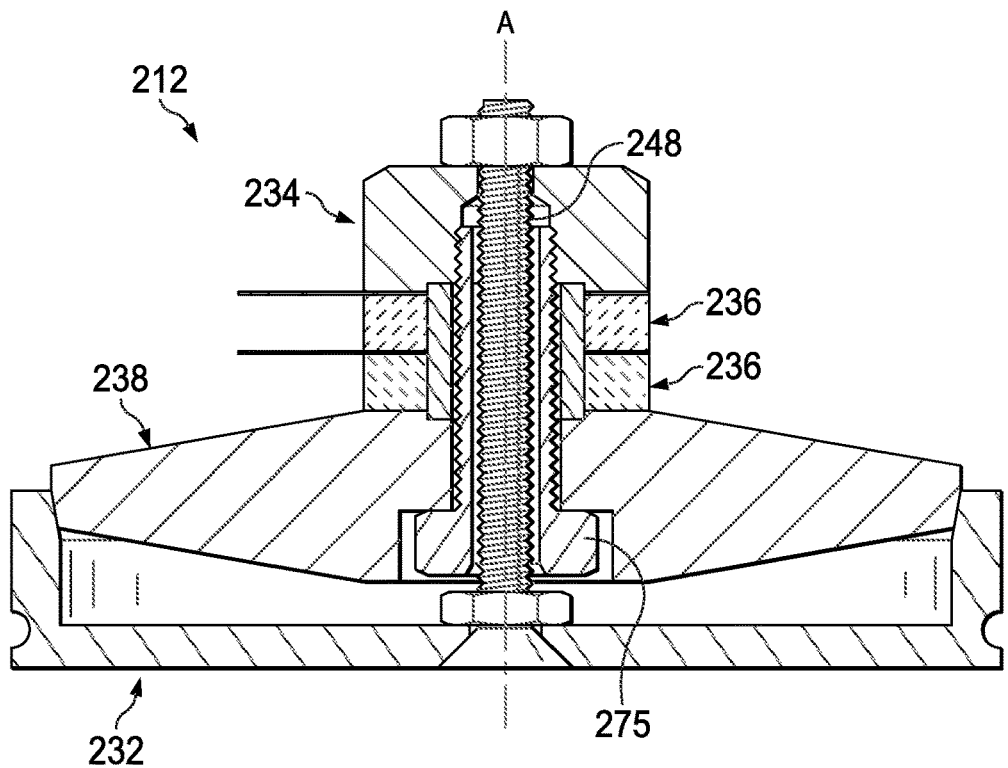
FIG. 10B is a cross sectional view taken along the line 10B-10B in FIG. 10A.

FIGS. 10A and 10B illustrate an alternative embodiment of a transducer 212 that is similar to, or the same in many respects as, the transducer 12 illustrated in FIGS. 6A and 6B. For example, the transducer 212 can include a backmass 234, a pair of piezoelectric rings 236, a shim 238, and a fastener 248. However, the transducer 212 can include a hollow fastener 275 that surrounds the fastener 248 and is threaded into the backmass 234 to facilitate compression of the piezoelectric rings 236 between the shim 238 and the backmass 234. The hollow fastener 244 can be countersunk into the shim 238.

Figure 11A:
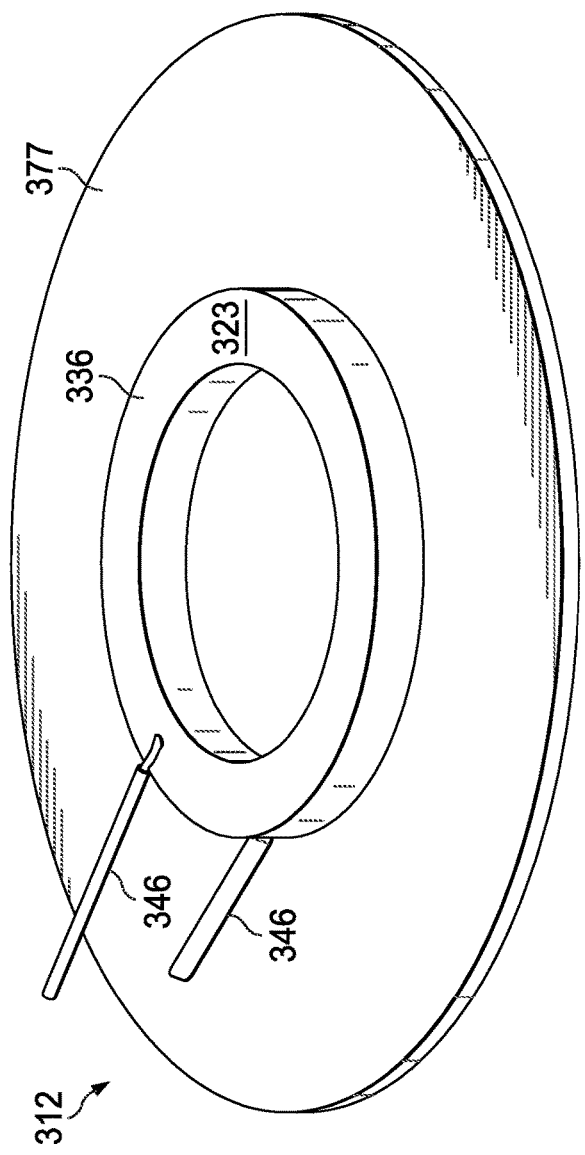
FIG. 11A is an isometric view depicting a transducer, in accordance with yet another embodiment.
Figure 11B:
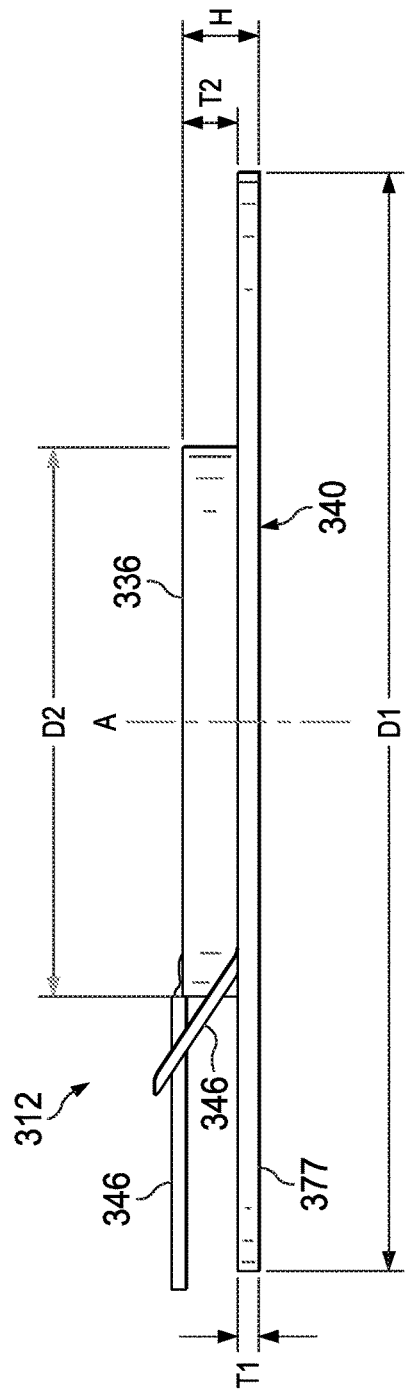
FIG. 11B is a side view depicting the transducer of FIG. 11A.
Figure 11C:
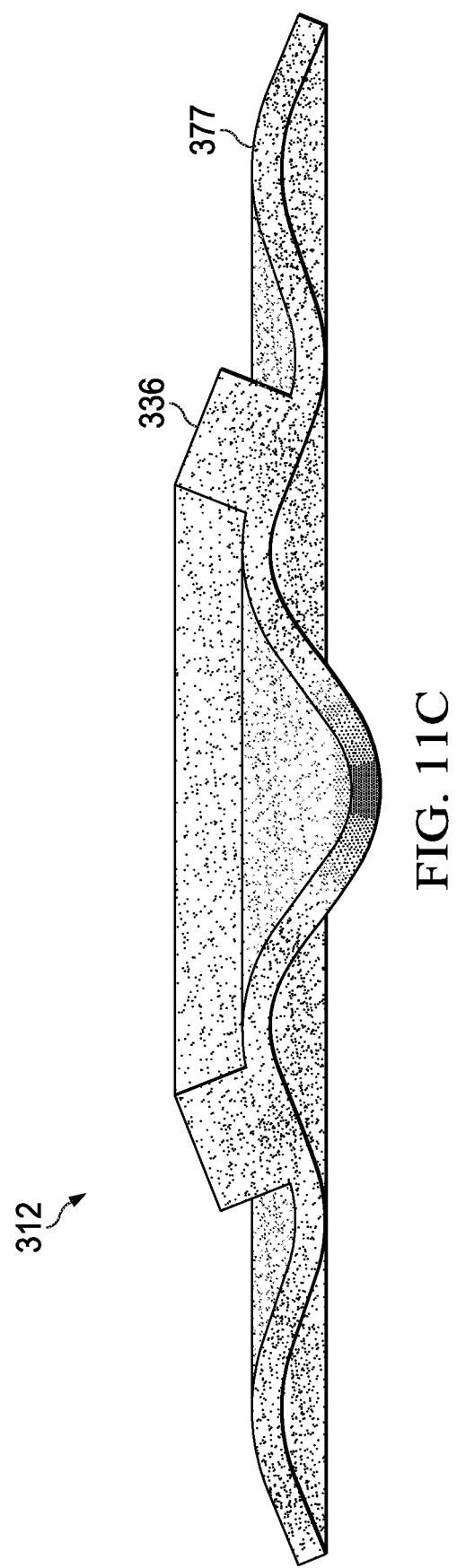
FIG. 11C is a cross sectional view depicting flexure of a radiating portion of the transducer of FIG. 11A in response to vibrational energy.

FIGS. 11A-11C illustrate an alternative embodiment of a transducer 312 that includes a piezoelectric ring 336 that is coupled to a radiant disc 377 on an opposite side of the radiant disc 377 as a radiating portion 340. In one embodiment, the piezoelectric ring 336 can be coupled to the radiant disc 377 with epoxy, or any of a variety of suitable alternative adhesives. In an alternative embodiment, the piezoelectric ring 336 can coupled to the radiant disc 377 via any of a variety of suitable alternative attachment techniques, such as, for example, with fasteners, via welding, or through an additive manufacturing technique. The piezoelectric ring 336 can be substantially coaxially located on the radiant disc 377. The radiant disc 377 can have a substantially flat profile and can have a diameter D1 and a thickness T1, The radiant disc 377 can be configured such that a ratio of the diameter D1 to the thickness T1 is between about 2:1 to about 200:1. A pair of electrodes 346 can be attached to opposing upper and lower surfaces (e.g., upper surface 323) of the piezoelectric ring 336 such that the electrodes 346 are spaced apart from each other along a centerline A that extends in the substantially the same direction as the thickness T1 and is substantially perpendicular to the diameter D1. The piezoelectric ring 336 can have a diameter D2 and a thickness T2. The piezoelectric ring 336 can be configured such that the diameter D2 is less than the diameter D1 of the radiant disc 377. In one embodiment, the ratio of the diameter D2 to the diameter D1 can be between about 1:1 to about 1:10. The piezoelectric ring 336 can also be configured such that the thickness T2 is greater than the thickness T1 of the radiant disc 377. In one embodiment, the ratio of the thickness T2 to the thickness T1 can be between about 1:6 to about 20:1. It is to be appreciated that the term disc can be understood to mean a substrate that is substantially continuous along its diameter. It is to be appreciated that although the electrodes 346 are shown to contact the upper and lower surfaces piezoelectric ring 336 other electrode arrangements or combinations thereof are contemplated. For example, in one embodiment, the electrodes can comprise a conductive film (or surface additives) that at least partially cover the upper and lower surfaces of the piezoelectric ring 336. In another embodiment, the radiating disc 377 can act as an electrode if it is made of a conductive material and has sufficient contact with the piezoelectric ring 336.

The piezoelectric ring 336 can be formed of a piezoelectric material such as piezoceramic, which can resonate (e.g., vibrate) in response to imparted electricity from the electrodes 346. In one embodiment, the radiant disc 377 can be formed of stainless steel. It is to be appreciated, however, that the piezoelectric ring 336 and the radiant disc 377 can be formed of any of a variety of suitable alternative materials. Arrangement of the piezoelectric ring 336 and the radiant disc 377 in this manner can provide a low profile for the transducer 312. The piezoelectric ring 336 can have a radial mode at the same frequency as the flexural resonance of the radiant disc 377. Furthermore, the radiant disc 377 can have a node that is centered on, near, or between, inner and outer diameters of the piezoelectric ring 336. A schematic representation of the flexure of a radiating portion 340 due to vibrational energy is shown in FIG. 11C.

Figure 11D:
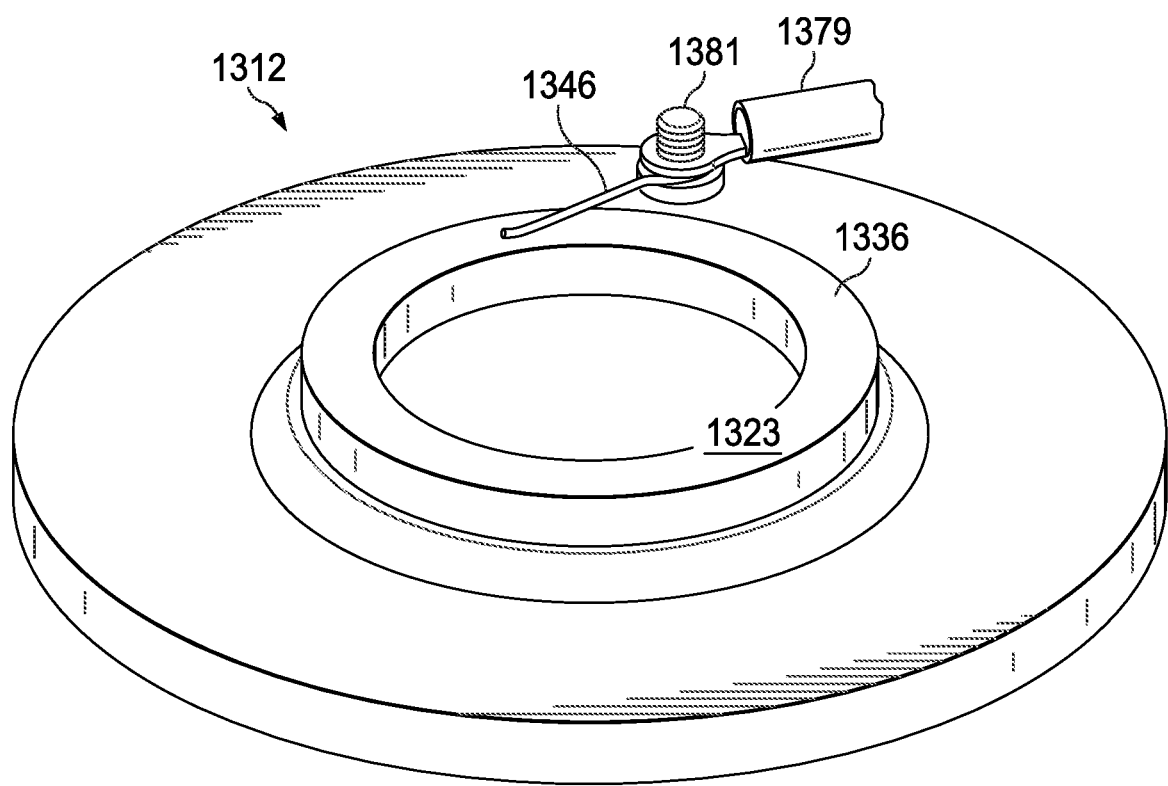
FIG. 11D is an isometric view depicting a transducer, in accordance with yet another embodiment

FIG. 11D illustrates an alternative embodiment of a transducer 1312 that is similar to, or the same in many respects as, the transducer 312 illustrated in FIGS. 11A and 11B. For example, the transducer 1312 can include a piezoelectric ring 1336 and an electrode 1346. However, the electrode 1346 can be formed of a spring material (e.g., a spring style lead) disposed adjacent to the piezoelectric ring 1336 and configured to biased the electrode 1346 against an upper surface 1323 of the piezoelectric ring 1336 with sufficient force to maintain contact with the piezoelectric ring 1336 while the transducer 1312 is vibrating. The long axis of the electrode 1346 can be either tangentially disposed with the piezoelectric ring 1336, radially disposed with the piezoelectric ring 1336, or at some angle therebetween. In addition, the electrode 1346 can be electrically coupled with a driver signal generator via a wire (not shown) that is coupled with a ring terminal 1379 attached to the wire. The electrode 1346 and the ring terminal 1379 can be secured together with a screw 1381.

Figure 12A:
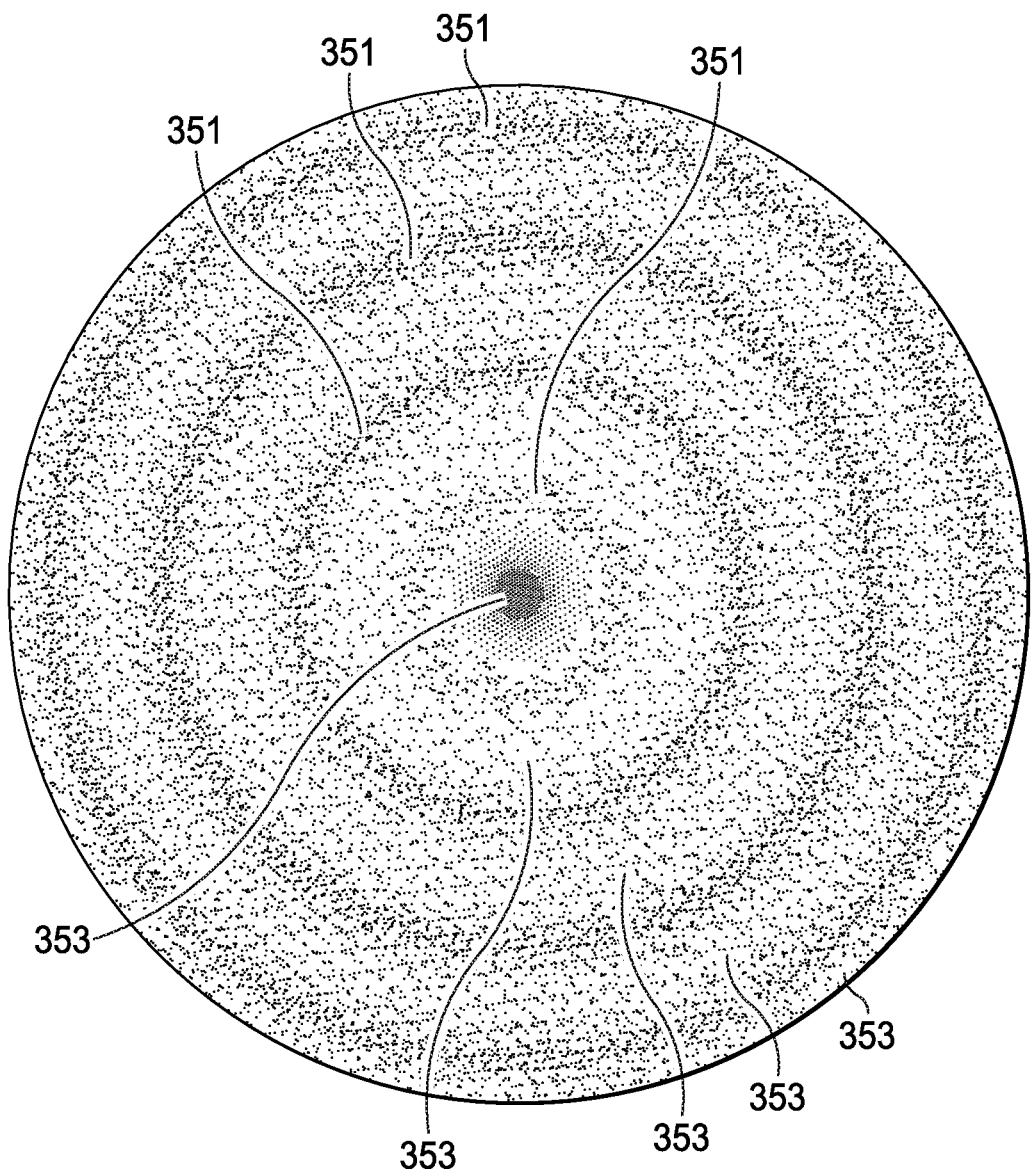
FIGS. 12A-12B depict a resonance pattern generated on a radiating portion of the transducer of FIGS. 11A-C.
Figure 12B:
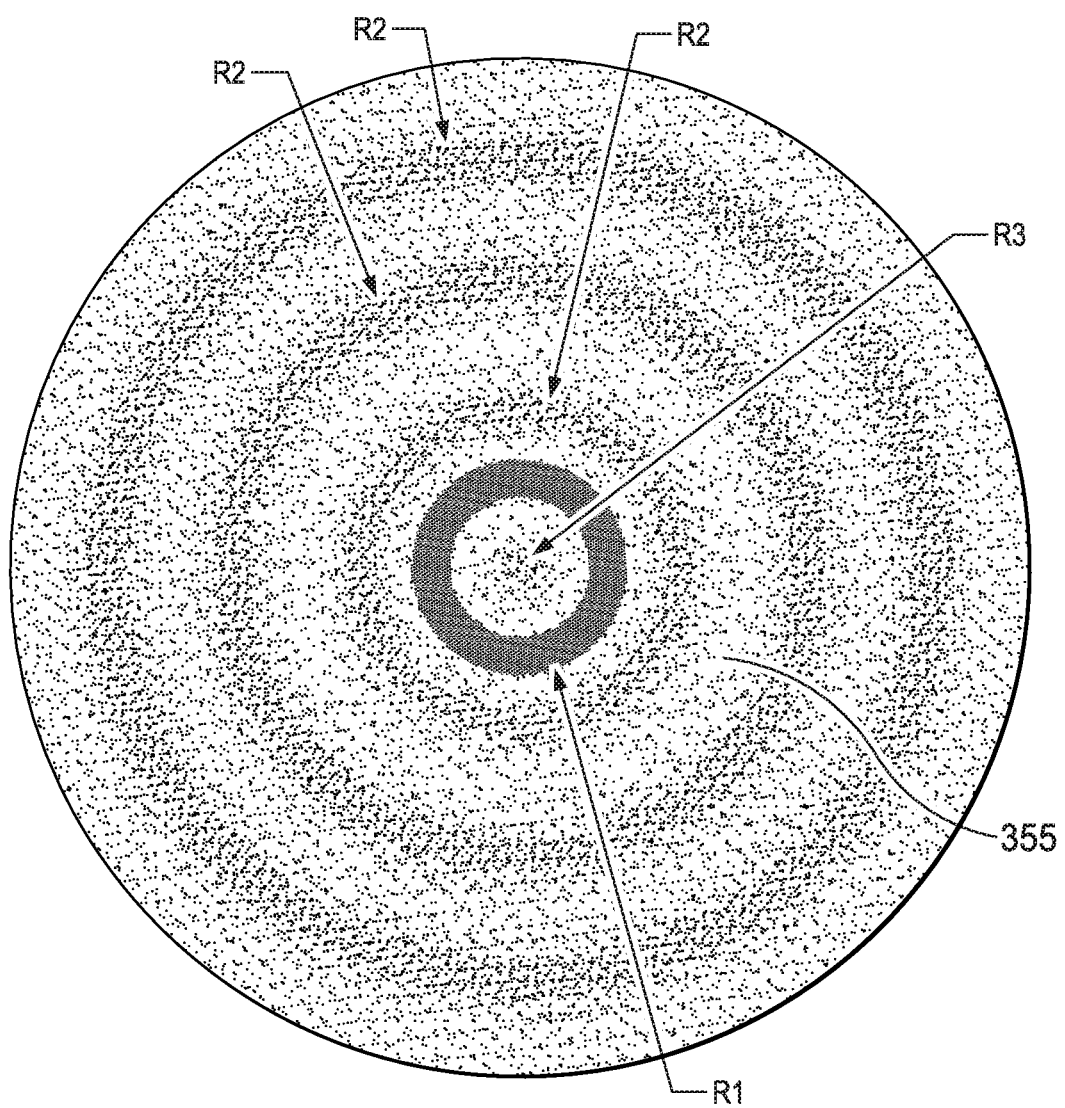

FIGS. 12A and 12B each illustrate an example resonance pattern that can be generated on the radiating portion 340 of the transducer 312. For example, FIG. 12A illustrates a resonance pattern at a flexural resonance and includes a plurality of radially concentric nodes 351 separated by radially concentric antinodes 353 (hereinafter "nodes" and "antinodes," respectively). The nodes 351 and antinodes 353 can manifest in the radiating portion 340 normal to the displacement of the radiating portion 340 (e.g., in the direction of the centerline A in FIG. 11B). The nodes 351 can correspond to minimal displacement (e.g., zero normal displacement) and the antinodes 353 can correspond to displacement peaks. The antinode 353 at the center of FIG. 12A represents a maximum normal displacement. FIG. 12B illustrates a resonance pattern indicating the ratio between radial and normal (out-of-plane) displacements at the same flexural resonance shown in FIG. 12A. An interior ring R1 can indicate a maximum ratio and a plurality of outer rings R2 and a dot R3 can indicate a minimum (e.g., zero) ratio. A piezoceramic material ring can be sized to be disposed, for example, at a ring diameter 355 (FIG. 12B), such that its radial mode is at the same frequency a flexural mode of the radiant disc 377 to create a mutually resonant system.

Figure 13A:
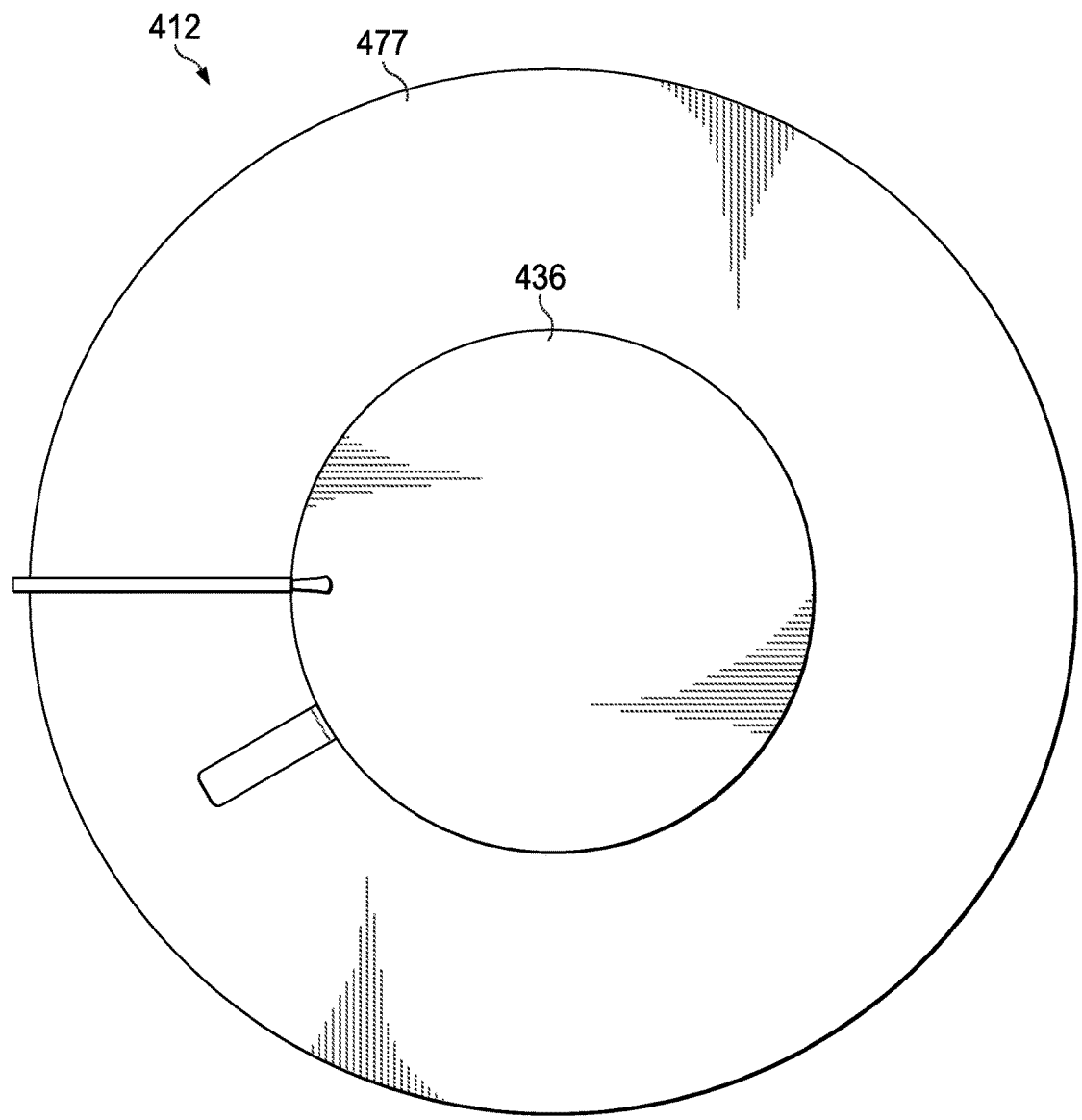
FIG. 13A is a top view depicting a transducer, in accordance with yet another embodiment.
Figure 13B:
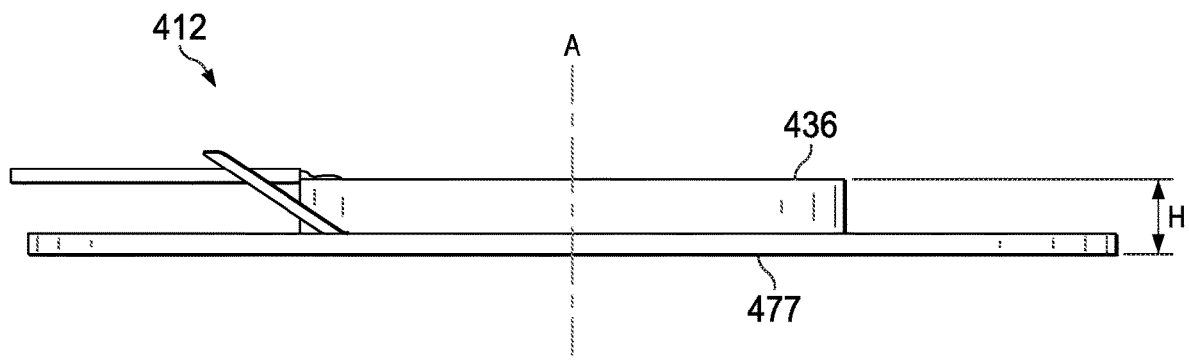
FIG. 13B is a side view depicting the transducer of FIG. 13A.
Figure 14A:
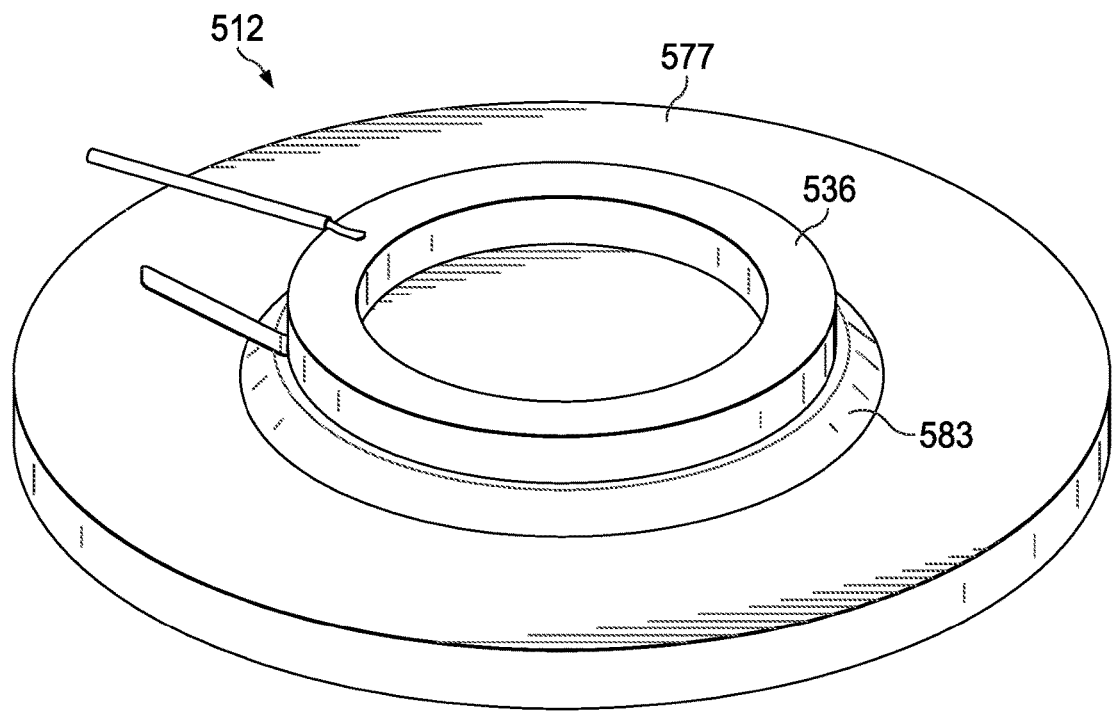
FIG. 14A is an isometric view depicting a transducer, in accordance with yet another embodiment.
Figure 14B:
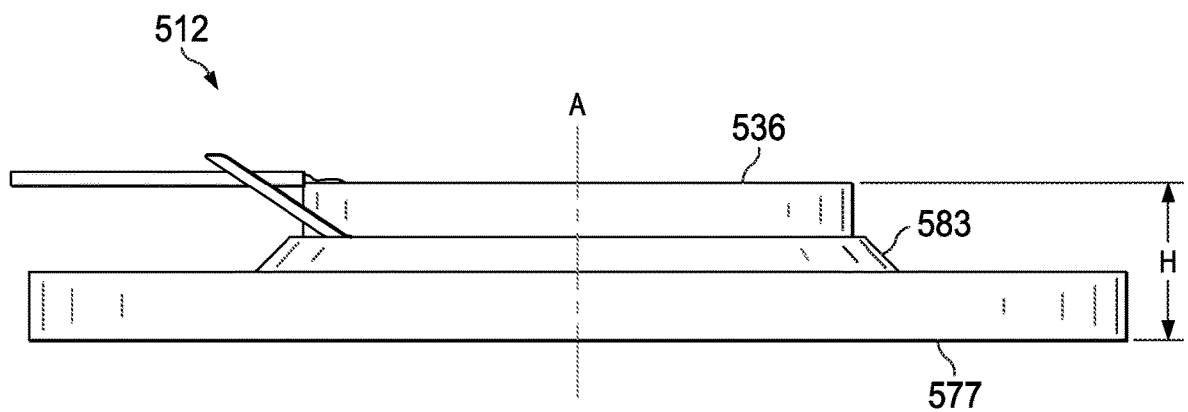
FIG. 14B is a side view depicting the transducer of FIG. 14A.
Figure 14C:
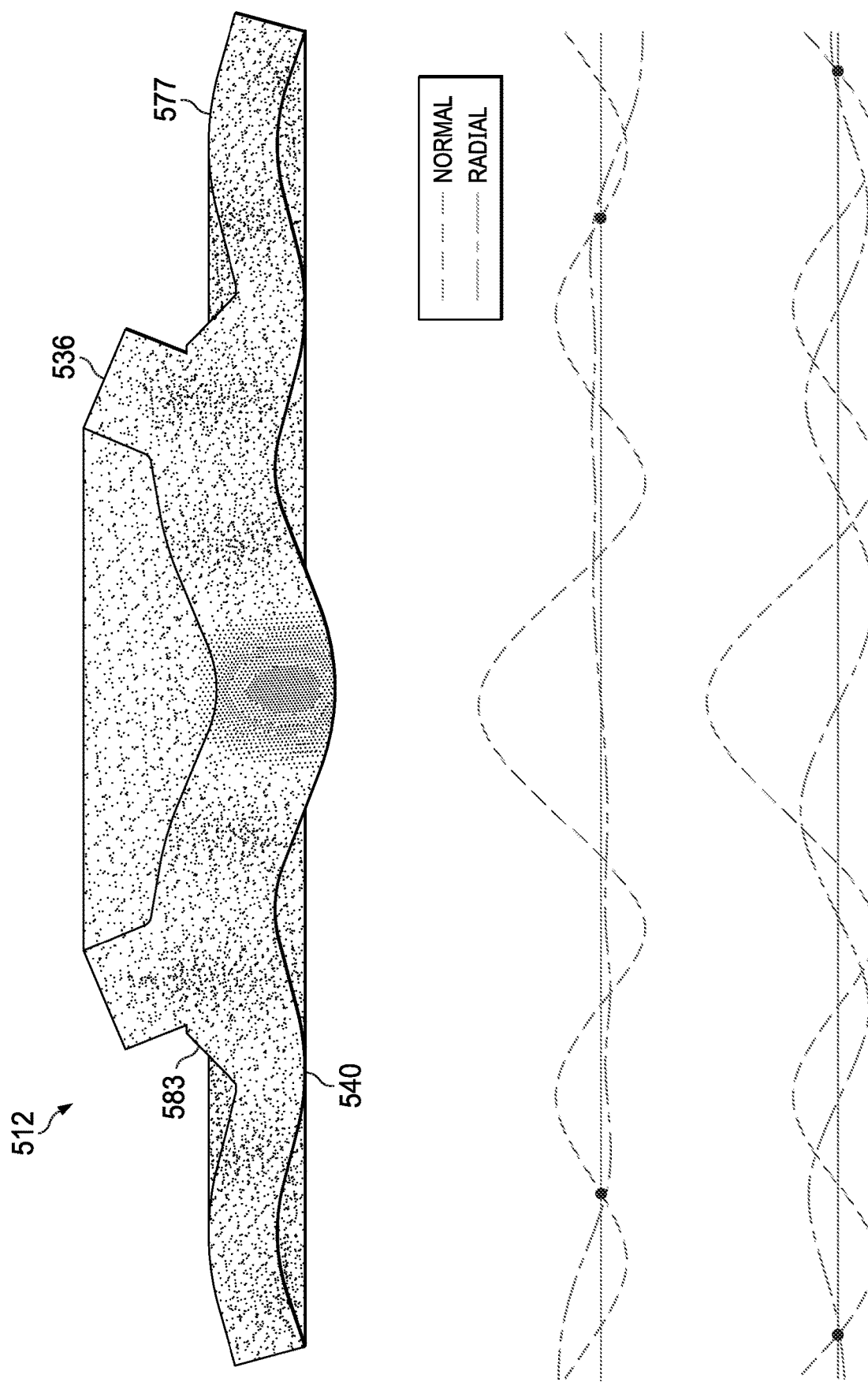
FIG. 14C is a cross sectional view depicting flexure of a radiating portion of the transducer of FIGS. 14A and 14B in response to vibrational energy.

FIGS. 13A and 13B illustrate an alternative embodiment of a transducer 412 that is similar to, or the same in many respects as, the transducer 312 illustrated in FIGS. 11A and 11B. For example, the transducer 412 can include a radiant disc 477. However, a piezoelectric disc 436 can be affixed to the radiant disc 477 in lieu of a piezoelectric ring (e.g., 336). FIGS. 14A and 14B illustrate an alternative embodiment of a transducer 512 that is similar to, or the same in many respects as, the transducer 312 illustrated in FIGS. 11A and 11B. For example, the transducer 512 can include piezoelectric ring 536 and a radiant disc 577. However, the radiant disc 577 can include a shoulder portion 583 to which the piezoelectric ring 536 is attached. The shoulder portion 583 can be frustoconically shaped and can be sized to be equal to or greater in diameter than an outer diameter of the piezoelectric ring 536 and can have relatively the same thickness as the piezoelectric ring 536. A schematic and graphical representation of the flexure of a radiating portion 540 of the transducer 512 due to vibrational energy is illustrated in FIG. 14C. In one embodiment, the height H of the transducer 512 can be less than about 0.7 inches, less than about 0.6 inches, or about 0.59 inches. The weight of the transducer 512 illustrated in FIGS. 14A and 14B can be less than about 8 ounces, and can be less than 7 ounces, and can be between about 5 and 7 ounces, and can be about 4.06 ounces. In one embodiment, the frequency of the transducer 512 can be about 21.8 kHz. In one embodiment, the impedance of the transducer 512 can be about 210 Ohms.

Figure 15A:
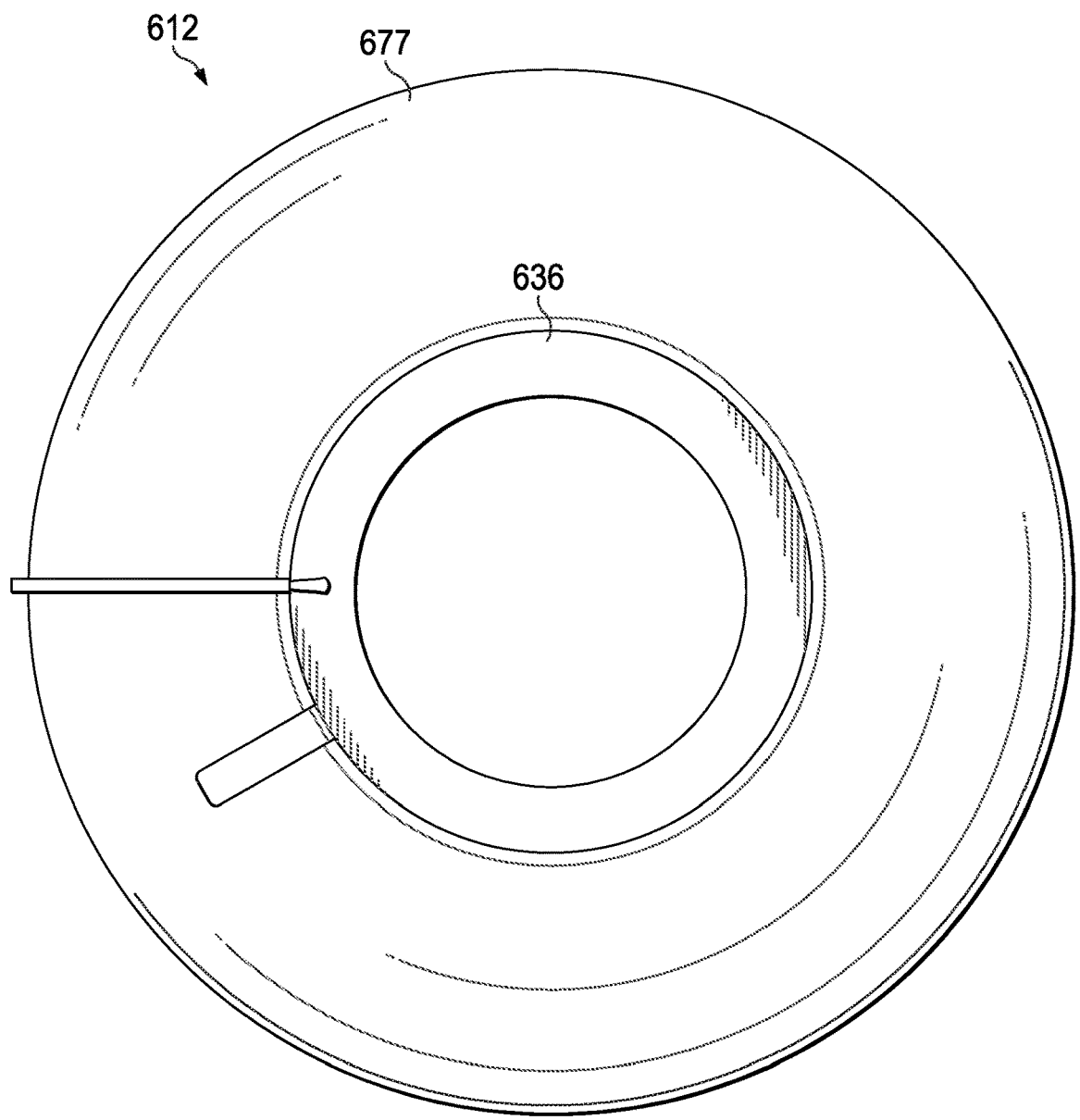
FIG. 15A is a top view depicting a transducer, in accordance with yet another embodiment.
Figure 15B:
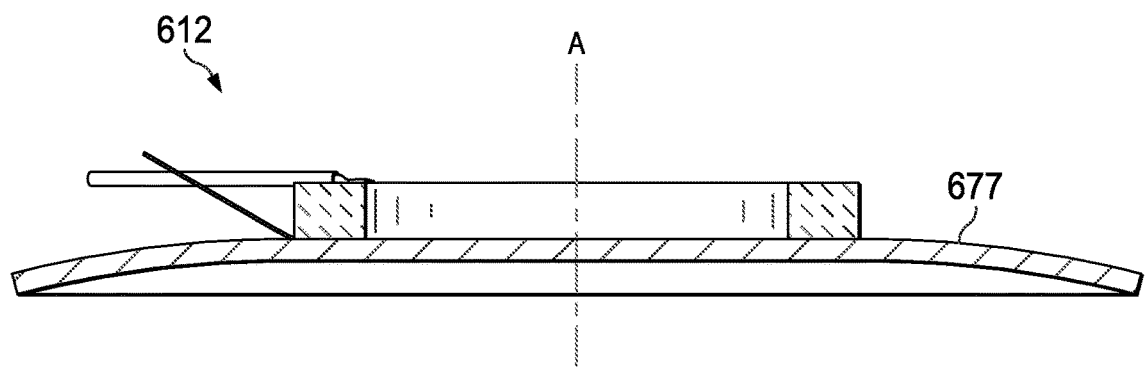
FIG. 15B is a side view depicting the transducer of FIG. 15A.

FIGS. 15A and 15B illustrate an alternative embodiment of a transducer 612 that is similar to, or the same in many respects as, the transducer 312 illustrated in FIGS. 11A and 11B. For example, the transducer 612 can include piezoelectric ring 636 and a radiant disc 677. The radiant disc 677, however, can be substantially convex shaped (when viewed along a centerline from the perspective of the piezoelectric ring 636) and can have a radius of curvature that is equal to or greater than an outer diameter of the piezoelectric ring 636.

Figure 16:
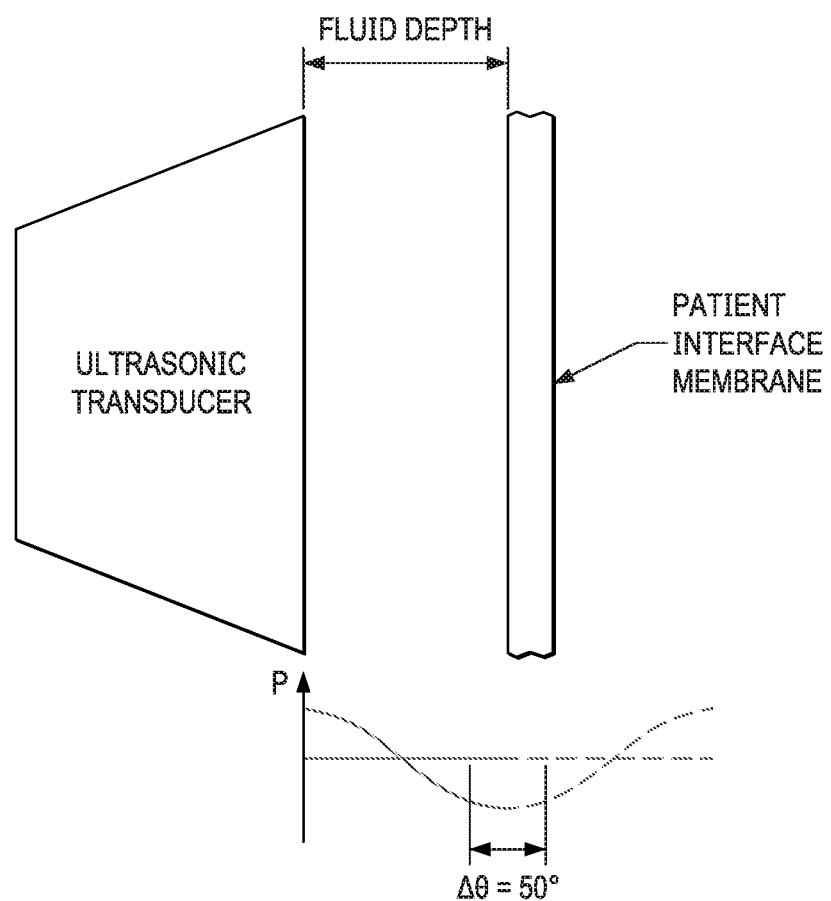
FIG. 16 is a schematic illustration of a relationship between a transducer and a patient interface membrane.

Referring now to FIG. 16, the fluid depth between the ultrasonic transducer and the patient contact interface can be an integer multiple of half-wavelengths of longitudinal pressure waves in the fluid. This permits an antinode to be present at the patient interface making displacement the highest and stress the lowest at the patient interface. In the pressure profile (P) for the fluid as shown in FIG. 16, the solid line indicates the first half-wave and the dashed line indicates a second half-wave. A tolerance (AO) of 50° centered on the antinode can be selected so that the amplitude at the interface is at least 90% of the antinode amplitude.

Figure 17:
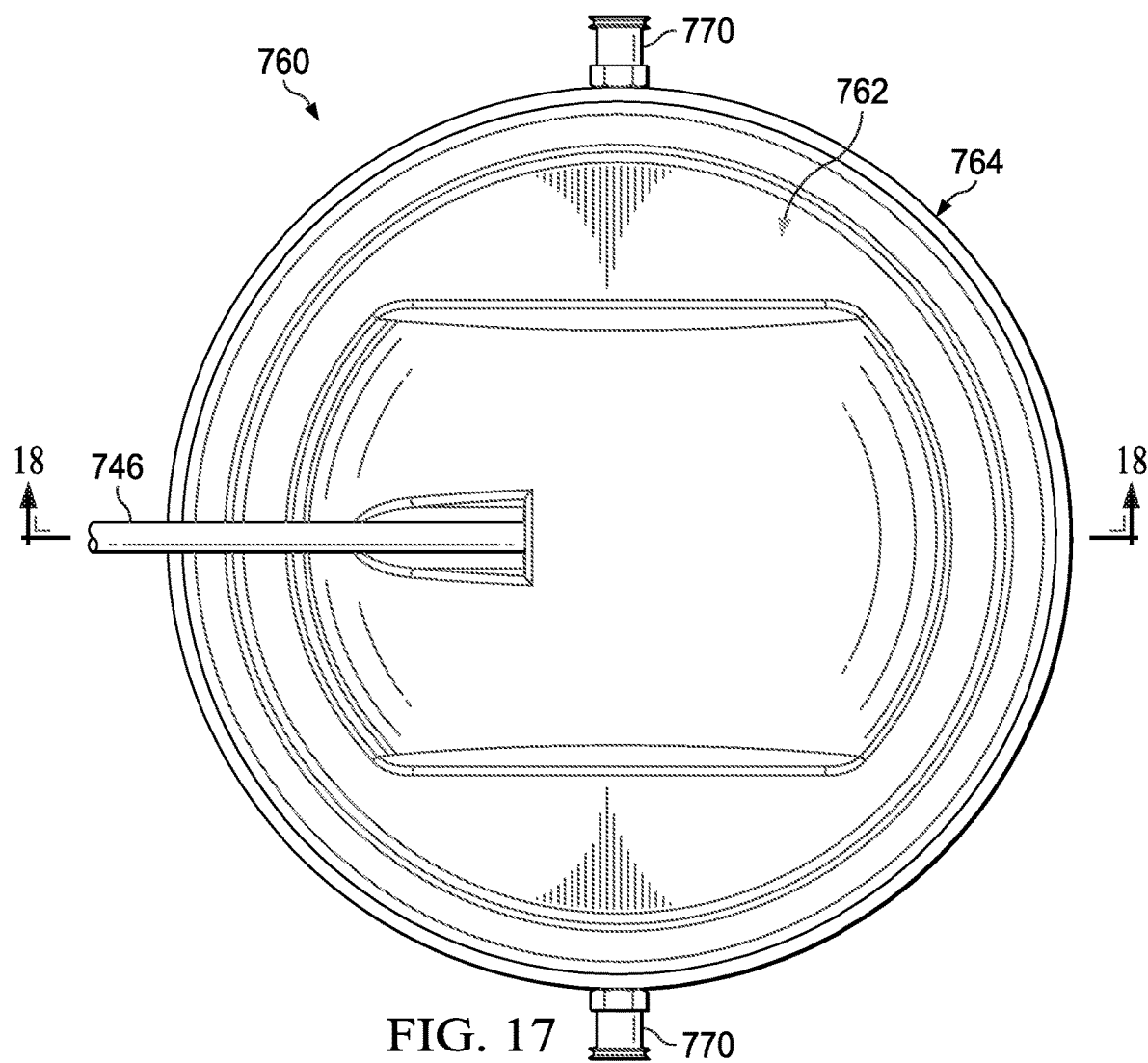
FIG. 17 is a top view depicting a housing, in accordance with one embodiment.
Figure 18:
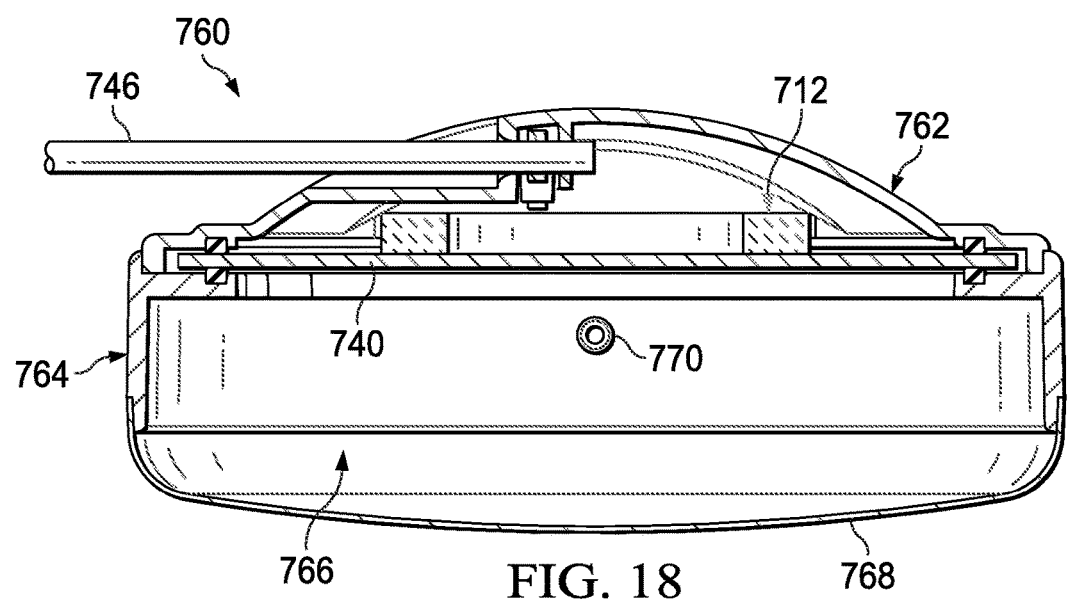
FIG. 18 is a cross sectional view taken along the line 18-18 in FIG. 17.

Referring now to FIGS. 17 and 18, one embodiment of a housing 760 is illustrated for housing a transducer 712. The transducer 712 is shown to be similar to the transducer 412 described above, but it is to be appreciated than any other type of transducer can be housed in the housing 760 or in a similar housing. The housing 760 can include an upper portion 762 and a lower portion 764 that are fluidly isolated from one another. The lower portion 764 can cooperate with the transducer 712 to define a fluid chamber 766. The transducer 712 can be disposed with its radiating portion 740 adjacent to the fluid chamber 766. Cooling fluid (not shown) can be provided in the fluid chamber 766 to facilitate cooling of the patient interface during operation of the transducer 712. The upper portion 762 and the lower portion 764 can be secured together with mating grooves or with any of a variety of suitable alternative securing arrangements (e.g., heat welded). Electrodes 746 can be bundled and routed through the upper portion 762 and to the transducer 712. The lower portion 764 can define a patient interface surface 768. In one embodiment, the housing 760 can be formed of a thermoplastic, but any of a variety of suitable alternative materials are contemplated.

The housing 760 can include a pair of fluid ports 770 that are disposed at opposing sides of the lower portion 764 of the housing 760 and are in fluid communication with the fluid chamber 766. A supply line (not shown) and a discharge line (not shown) of a fluid source (not shown) can be fluidly coupled with respective ones of the fluid ports 770 such that the fluid source can circulate cooling fluid through the fluid chamber 766.

Figure 19:
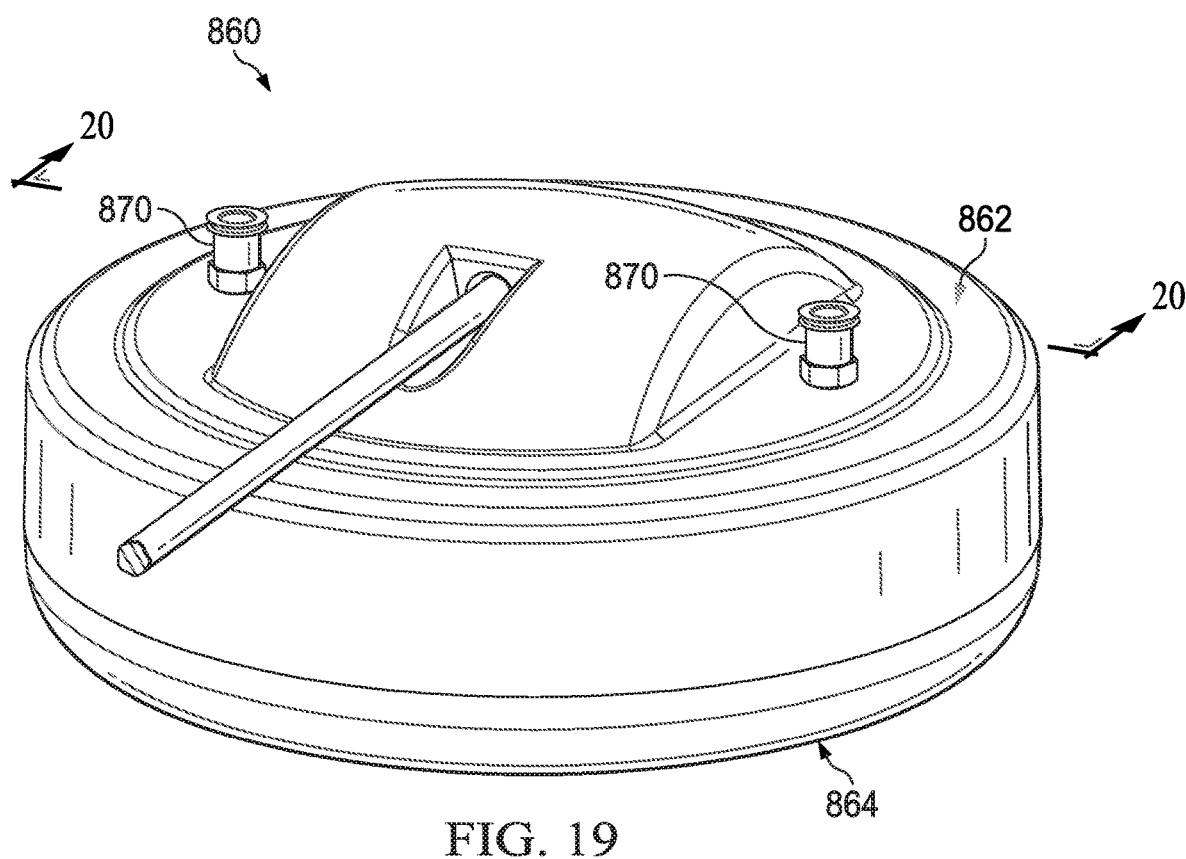
FIG. 19 is an isometric view depicting a housing, in accordance with another embodiment.
Figure 20:
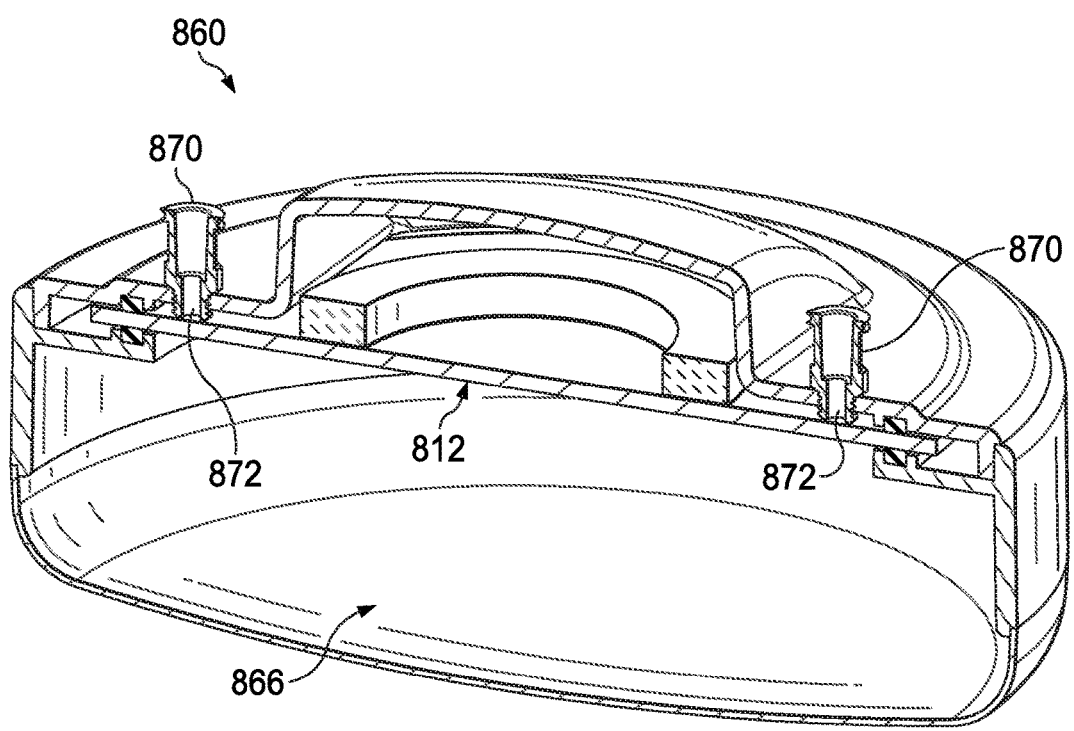
FIG. 20 is a cross sectional view taken along the line 20-20 in FIG. 19.

FIGS. 19 and 20 illustrate an alternative embodiment of a housing 860 that is similar to, or the same in many respects as, the housing 760 illustrated in FIGS. 17 and 18. For example, the housing 860 can include an upper portion 862 and a lower portion 864 that cooperate to define a fluid chamber 866. A transducer 812 can be disposed in the fluid chamber 866. However, the housing 860 can include a pair of fluid ports 870 that are disposed on top of the upper portion 862. The transducer 812 can define a pair of openings 872 that are registered with the fluid ports 870 to allow cooling fluid provided to/from the fluid ports 870 to pass through the transducer 812.

Figure 21:
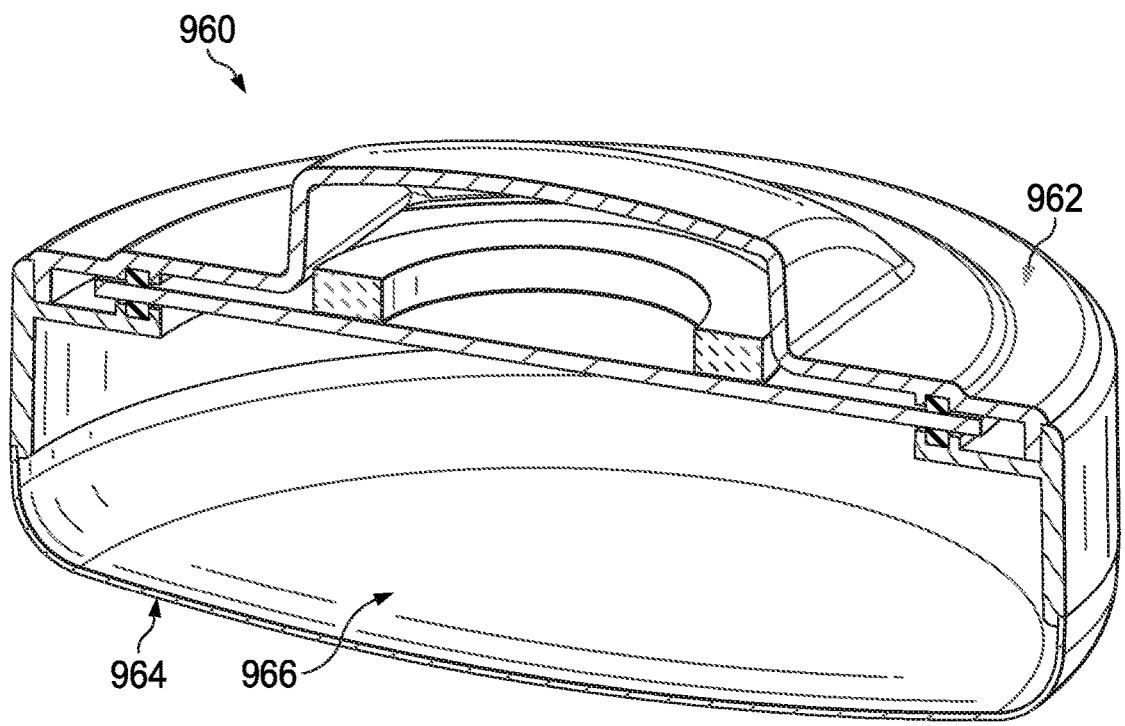
FIG. 21 is an isometric cross sectional view depicting a housing, in accordance with yet another embodiment.

FIG. 21 illustrates an alternative embodiment of a housing 960 that is similar to, or the same in many respects as, the housing 760 illustrated in FIGS. 17 and 18. For example, the housing 960 can include an upper portion 962 and a lower portion 964 that cooperate to define a fluid chamber 966. However, the housing 960 can be devoid of fluid ports (e.g., 770, 870) such that the fluid chamber 966 is self-contained. In one embodiment, the housing 960 can be configured to facilitate selective degassing of the cooling fluid contained in the fluid chamber 966.

Figure 22:
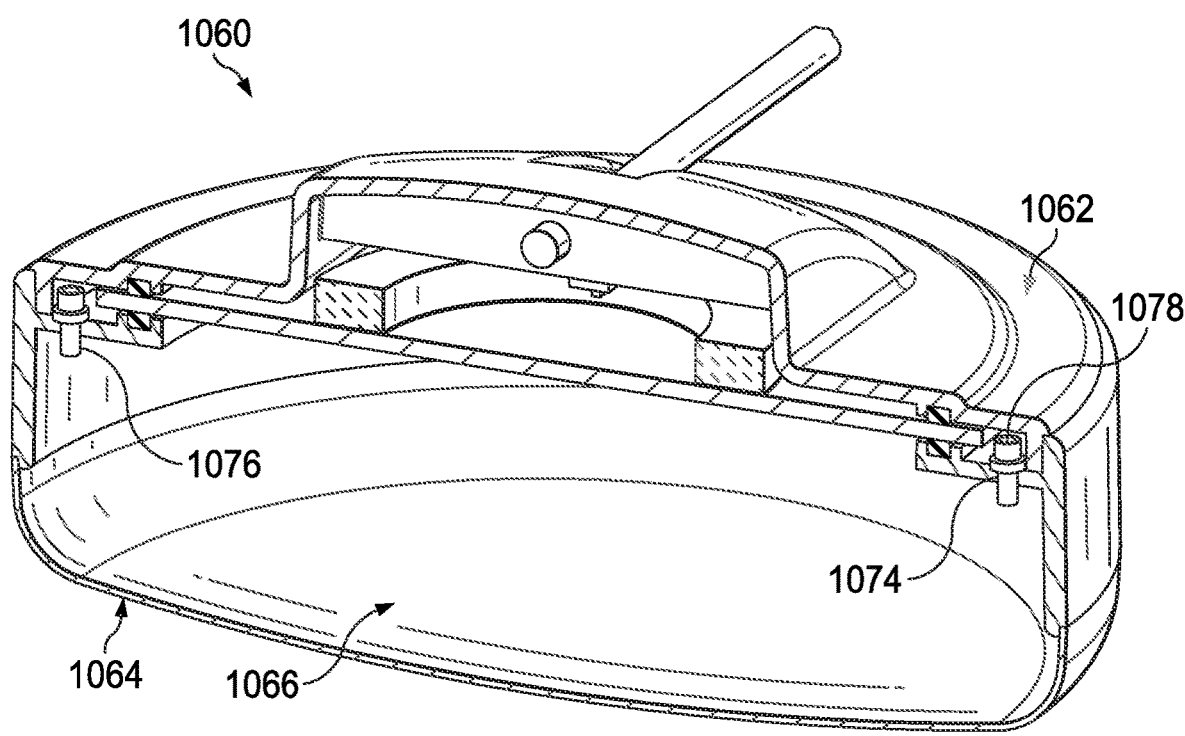
FIG. 22 is an isometric cross sectional view depicting a housing, in accordance with yet another embodiment.

FIG. 22 illustrates an alternative embodiment of a housing 1060 that is similar to, or the same in many respects as, the housing 960 illustrated in FIG. 21. For example, the housing 1060 can include an upper portion 1062 and a lower portion 1064 that cooperate to define a fluid chamber 1066. The housing 1060, however, can include a suction port 1074, a return port 1076, tubing 1078, and a pump (not shown) that cooperate to facilitate internal circulation of the cooling fluid in the fluid chamber 1066. In one embodiment, a heat exchanger (not shown) can be included.

Figure 23:
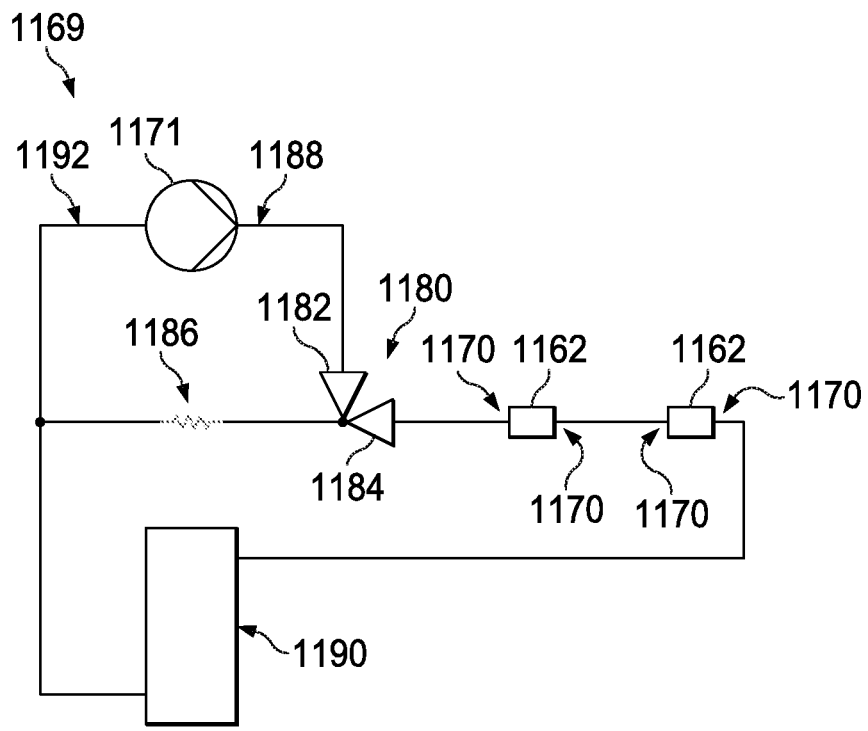
FIG. 23 is a schematic view depicting a recirculation system in fluid communication with a fluid chamber, in accordance with one embodiment.

Referring now to FIG. 23, an alternative embodiment of a recirculation system 1169 is illustrated that is similar to the recirculation system 69 illustrated in FIGS. 6A and 6B. For example, the recirculation system 1169 can be in fluid communication with a fluid chamber 1162 via fluid ports 1170. The recirculation system 1169 can include a pump 1171 that circulates the cooling medium through the fluid chambers 1162 of a pair of transducers to facilitate the removal of heat from the fluid chambers 1162 by cooling the fluid medium. However, the recirculation system 1169 can include a relief valve 1180 that includes an input port 1182, an output port 1184, and a bypass port 1186. The input port 1182 can be in fluid communication with an output port 1188 of the pump 1171 such that the relief valve 1180 is downstream of the pump 1171. The output port 1182 can be in fluid communication with the fluid chambers 1162 which can be in fluid communication with a fluid reservoir 1190. The bypass port 1186 can be in fluid communication with an input port 1192 of the pump 1171.

The relief valve 1180 can be operable in either a normal mode or a bypass mode. When the relief valve 1180 is in the normal mode, the input port 1182 and the output port 1184 can be in fluid communication with each other and disconnected from the bypass port 1186 to facilitate dispensation of the cooling fluid through the output port 1184, through the fluid chambers 1162 and to the fluid reservoir 1190. When the relief valve 1180 is in the bypass mode, the input port 1182 and the bypass port 1186 can be in fluid communication with each other to facilitate dispensation of the cooling fluid through the bypass port 1186 and away from the fluid chambers 1162 to effectively bypass the fluid chambers 1162 and the fluid reservoir 1190.

The relief valve 1180 can be operated in either the normal mode or the bypass mode as a function of the pressure of the cooling fluid in at least one of the fluid chambers 1162 as compared to a threshold pressure. If the pressure of the cooling fluid is below the threshold pressure, the relief valve 1180 can operate in the normal mode. However, if the pressure of the cooling fluid in one or more of the fluid chambers 1162 is above the threshold pressure (e.g., an overpressure condition), the relief valve 1180 can operate in the bypass mode to allow the cooling fluid to bypass the fluid chambers 1162. The relief valve 1180 can accordingly redirect the cooling fluid away from the fluid chambers 1162 when the fluid circuit for the fluid chambers 1162 becomes blocked (e.g., kinked) or otherwise malfunctions enough to cause the pressure in the fluid chambers 1162 to be excessive.

A pressure sensor (not shown) can be disposed in each of the fluid chambers 1162 and configured to detect the pressure of the cooling fluid in the fluid chambers 1162. The pressure sensors can relay the detected pressure to a controller (not shown) that can facilitate operation of the relief valve 1180 in either the normal mode or the bypass mode depending upon whether the detected pressure exceeds the threshold pressure. In one embodiment, the pressure sensors can comprise pressure transducers, although any of a variety of suitable alternative pressure sensing devices are contemplated.

Figure 24:
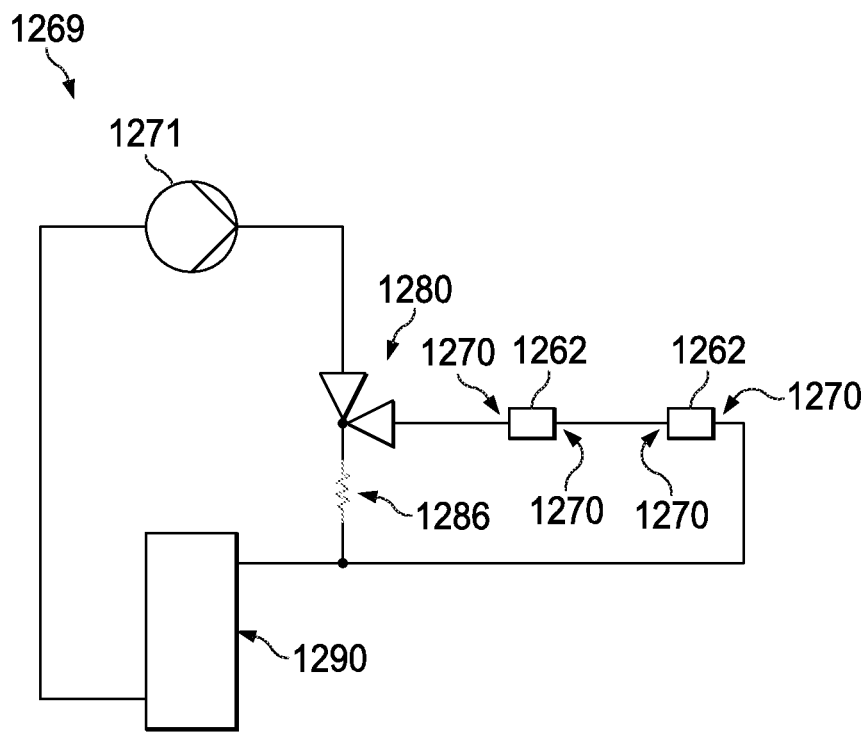
FIG. 24 is a schematic view depicting a recirculation system in fluid communication with a fluid chamber, in accordance with another embodiment

Referring now to FIG. 24, an alternative embodiment of a recirculation system 1269 is illustrated that is similar to the recirculation system 1169 illustrated in FIG. 23. For example, the recirculation system 1269 can be in fluid communication with a pair of fluid chambers 1262 via fluid ports 1270. The recirculation system 1269 can include a pump 1271 that circulates the cooling medium through the fluid chambers 1262. A relief valve 1280 can include a bypass port 1286. The bypass port 1286, however, can be in fluid communication with the fluid chamber 1262 such that when the relief valve 1280 is in the bypass mode, cooling fluid from the pump 1271 can bypass the fluid chambers 1262 and can flow into the fluid chamber 1290.

While the apparatuses described above can be used for dialysis and mitigating nephrotoxicity of contrast agents and other materials, the structures and methods described herein may find a variety of additional applications. For example, chronic kidney disease is often characterized by an activated sympathetic nervous system (SNS), which may contribute to the pathogenesis of hypertension. Kidney injury and ischemia increase afferent sympathetic nerve activity to the central nervous system (CNS) and result in increased sympathetic nervous system activation, and increased blood pressure. The increased catecholamines from SNS activation can lead to further injury to the kidney in CKD.

The nitric oxide system is a natural antagonist of catecholamines. A state of nitric oxide deficiency is characteristic in CKD patients. Standard hemodialysis causes sympathetic activation. Advantageously, repeated application of LOFUS to patients with CKD may result in a slowing of the progression of CKD, and one strategy to improve kidney oxygenation via increased vasculogenesis might be a key component of this protection. Such repeated LOFUS may also provide a reduction in blood pressure in hypertensive patients with CKD (and may also be effective as a noninvasive means of blood pressure reduction in the general population with drug resistant hypertension). Hence, LOFUS may be administered up to daily for up to several hours per day for up to weeks (or even months), using the energy characteristics already described. In one exemplary approach, thirty-five, one-hour treatment periods with application of LOFUS may be performed for a patient with CKD over about 7 weeks to slow CKD progression. This may invoke the anti-inflammatory properties of NO and ischemia treating properties of NO (vasculogenesis and cell protection) to provide sustained beneficial effects following a course of repeated therapy. The result may allow a prolongation of the need for commencement of dialysis.

The foregoing description of embodiments and examples has been presented for purposes of illustration and description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent devices by those of ordinary skill in the art. Rather, it is hereby intended that the scope be defined by the claims appended hereto. Also, for any methods claimed and/or described, regardless of whether the method is described in conjunction with a flow diagram, it should be understood that unless otherwise specified or required by context, any explicit or implicit ordering of steps performed in the execution of a method does not imply that those steps must be performed in the order presented and may be performed in a different order or in parallel.

What is claimed is:

1. An ultrasound transducer comprising: a backmass; a frontmass comprising a radiating portion and a pair of sidewalls extending from the radiating portion; a shim coupled with the sidewalls of the frontmass and spaced from the radiating portion such that the shim and the frontmass cooperate to define an interior chamber; a pair of piezoelectric elements that are stacked together and sandwiched between the backmass and the shim; a pair of electrodes, each electrode being electrically coupled with at least one of the piezoelectric elements and configured for electrical coupling with a driving signal generator to receive a driving signal therefrom; a fastener that extends through each of the backmass, the pair of piezoelectric elements, the shim, and the frontmass and facilitates compression of each of the backmass, the pair of piezoelectric elements, the shim, and the frontmass together, wherein the piezoelectric elements are configured to generate ultrasonic energy in response to the driving signal that is transmitted through the fastener to the radiating portion and through the shim and the sidewalls to the radiating portion to collectively cause the radiating portion to resonate at a flexural resonance and frequency.

2. The ultrasound transducer of claim 1 further comprising a nut and wherein the fastener is threadably coupled with the nut to facilitate compression of each of the backmass, the pair of piezoelectric elements, the shim, and the frontmass together.

3. The ultrasound transducer of claim 1 wherein the fastener is threadably coupled with backmass to facilitate compression of each of the backmass, the pair of piezoelectric elements, the shim, and the frontmass together.

4. The ultrasound transducer of claim 1 further comprising a nut and a hollow fastener, wherein:
the fastener is threadably coupled with the nut; and
the hollow fastener is threadably coupled with the backmass.

5. The ultrasound transducer of claim 1 wherein the fastener defines a centerline and each of the backmass, the pair of piezoelectric elements, the shim, and the frontmass are coaxially arranged along the centerline.

6. The ultrasound transducer of claim 1 further comprising a nut threadably coupled with the fastener, wherein the nut is interposed between the shim and the radiating portion and facilitates securement therebetween.

7. The ultrasound transducer of claim 1 wherein the shim has a tapered profile.

8. The ultrasound transducer of claim 1 wherein the at least one piezoelectric element comprises a piezoelectric ring.

9. An ultrasound transducer comprising:
a radiant disc comprising a radiating portion, a first thickness, and a first diameter and defining a centerline that extends in substantially the same direction as the first thickness and is substantially perpendicular to the first diameter;
a piezoelectric element coupled with the radiant disc on an opposite side as the radiating portion;
a pair of electrodes, each electrode being electrically coupled with the piezoelectric element and configured for electrical coupling with a driving signal generator to receive a driving signal therefrom, wherein:
the piezoelectric element is configured to generate ultrasonic energy in response to the driving signal that is transmitted through the radiating portion and to cause the radiating portion to resonate at a flexural resonance and frequency; and
the first diameter is greater than the first thickness.

10. The ultrasound transducer of claim 9 wherein a ratio of the first diameter to the thickness T1 is between about 2:1 to about 200:1.

11. The ultrasound transducer of claim 9 wherein the piezoelectric element comprises a second diameter that is less than or equal to the first diameter.

12. The ultrasound transducer of claim 11 wherein a ratio of the second diameter to the first diameter is between about 1:1 to about 1:20.

13. The ultrasound transducer of claim 9 wherein the piezoelectric element comprises a second thickness that is greater than the first thickness.

14. The ultrasound transducer of claim 9 wherein the piezoelectric element comprises one or more of a piezoelectric ring and a piezoelectric disc.

15. The ultrasound transducer of claim 9 wherein the radiant disc is convex shaped.

16. The ultrasound transducer of claim 15 wherein the radiant disc comprises a flexural node provided on the radiating portion and having a diameter that is greater than an inner diameter of the piezoelectric ring and less than an outer diameter of the piezoelectric element.

17. The ultrasound transducer of claim 9 wherein one of the electrodes comprises a spring style electrode that is configured for biasing against the piezoelectric element that creates and maintains contact by a force generated through the deformation of the lead.

18. An assembly comprising:
a transducer comprising a piezoelectric element and radiating portion coupled with the piezoelectric element, the radiating portion being configured to resonate at a flexural resonance and frequency in response to a driving signal imparted to the piezoelectric element; and
a housing coupled with the transducer and cooperating with the transducer to define a fluid chamber for coupling fluid, the housing comprising a patient interface configured to interface with a patient's skin during treatment, the patient interface being spaced from the radiating portion by a fluid depth that is a multiple of a quarter wavelength of sound in the coupling fluid at the frequency.

19. The assembly of claim 18 wherein the patient interface comprises a flexible membrane.

20. An ultrasound energy delivery system comprising:
a transducer comprising a radiating portion configured to resonate at a flexural resonance and frequency in response to a driving signal;
a housing coupled with the transducer and cooperating with the radiating portion to define a fluid chamber;
a recirculation system in fluid communication with the fluid chamber, the recirculation system comprising:
a pump comprising a first input port and a first output port, the first input port being in fluid communication with the fluid chamber;
a relief valve comprising a second input port, a second output port, and a bypass port, the second input port being in fluid communication with the first output port;
a distribution line in fluid communication with each of the second output port and the fluid chamber, wherein:
the relief valve is operable in one of a normal mode and a bypass mode;
when the relief valve is in the normal mode, the second input port and the second output port are in fluid communication with each other to facilitate dispensation of cooling fluid through the distribution line and to the fluid chamber;

when the relief valve is in the bypass mode, the second input port and the bypass port are in fluid communication with each other to facilitate dispensation of the cooling fluid through the bypass port and away from the distribution line.

21. The ultrasound energy delivery system of claim 20 wherein the relief valve is operable in either the normal mode or the bypass mode as a function of a pressure of the cooling fluid in the distribution line.

22. The ultrasound energy delivery system of claim 21 further comprising a pressure sensor associated with the distribution line and configured to detect the pressure of the cooling fluid in the distribution line to facilitate operation of the relief valve in either the normal mode or the bypass mode.

23. The ultrasound energy delivery system of claim 20 wherein the bypass port is in fluid communication with at least one of the first input port and the fluid chamber.

\* \* \* \* \*